United States Patent
Howell et al.

(10) Patent No.: US 11,826,526 B2
(45) Date of Patent: Nov. 28, 2023

(54) SPLITABLE CATHETER DOCKING STATION SYSTEM AND METHOD

(71) Applicant: Bard Access Systems, Inc., Salt Lake City, UT (US)

(72) Inventors: Glade H. Howell, Draper, UT (US); Zachary S. Hastings, Sterling, MD (US); Kent Diasabeygunawardena, Nashua, NH (US); Jon B. Taylor, Groton, MA (US); Taylor C. Tobin, Nashua, NH (US); Jacquelyn N. Phelps, Cambridge, MA (US); Daniel Hamilton, Mount Vernon, MA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 33 days.

(21) Appl. No.: 17/156,252

(22) Filed: Jan. 22, 2021

(65) Prior Publication Data

US 2021/0228843 A1  Jul. 29, 2021

Related U.S. Application Data

(60) Provisional application No. 62/965,064, filed on Jan. 23, 2020.

(51) Int. Cl.
*A61M 25/06* (2006.01)
*A61M 25/09* (2006.01)
*A61M 29/00* (2006.01)

(52) U.S. Cl.
CPC .... *A61M 25/0606* (2013.01); *A61M 25/0631* (2013.01); *A61M 25/0693* (2013.01);
(Continued)

(58) Field of Classification Search
CPC ........ A61M 2209/086; A61M 25/0606; A61M 25/0631; A61M 25/09; A61M 25/0693;
(Continued)

(56) References Cited

U.S. PATENT DOCUMENTS

| | | |
|---|---|---|
| 1,013,691 A | 1/1912 | Shields |
| 3,225,762 A | 12/1965 | Guttman |

(Continued)

FOREIGN PATENT DOCUMENTS

| | | |
|---|---|---|
| DE | 202012006191 U1 | 7/2012 |
| EP | 0653220 A1 | 5/1995 |

(Continued)

OTHER PUBLICATIONS

PCT/US2020/048583 filed Aug. 28, 2020 International Search Report and Written Opinion dated Nov. 13, 2020.
(Continued)

*Primary Examiner* — Katherine H Schwiker
*Assistant Examiner* — Robert F Allen
(74) *Attorney, Agent, or Firm* — Rutan & Tucker LLP

(57) ABSTRACT

Disclosed is a two-step rapid insertion central catheter ("RICC") system that can include an introducer placement system, a docking station and a catheter placement system. The introducer placement system can place an introducer within a vasculature, which is supported by a docking station that detaches from a distal end of the introducer placement system. A catheter placement system can be configured to couple with the docking station, and a catheter can be advanced through the introducer into the vasculature. The introducer can then be split and retracted before the catheter placement system disengages the docking station. The docking station can be configured to split and disengage from the catheter. The RICC system can include a guidewire hub to prevent guidewire embolisms, collapsible sterile barriers to
(Continued)

prevent contamination, and locking features to prevent premature advancement of guidewires, dilators and the like.

23 Claims, 11 Drawing Sheets

(52) U.S. Cl.
CPC ............ *A61M 25/09* (2013.01); *A61M 29/00* (2013.01); *A61M 2209/086* (2013.01)

(58) Field of Classification Search
CPC ........ A61M 29/00; A61M 2025/09125; A61M 2025/028; A61M 2025/0117; A61M 25/02; A61M 25/01; A61M 25/0668; A61M 25/09041; A61M 25/0662; A61M 25/065; A61M 2025/0183
See application file for complete search history.

(56) References Cited

U.S. PATENT DOCUMENTS

| | | | |
|---|---|---|---|
| 3,382,872 A | 5/1968 | Rubin | |
| 3,570,485 A | 3/1971 | Reilly | |
| 3,890,976 A | 6/1975 | Bazell et al. | |
| 4,205,675 A | 6/1980 | Vaillancourt | |
| 4,292,970 A | 10/1981 | Hession, Jr. | |
| 4,468,224 A | 8/1984 | Enzmann et al. | |
| 4,525,157 A | 6/1985 | Vaillancourt | |
| 4,581,019 A | 4/1986 | Curelaru et al. | |
| 4,594,073 A | 6/1986 | Stine | |
| 4,702,735 A | 10/1987 | Luther et al. | |
| 4,743,265 A | 5/1988 | Whitehouse et al. | |
| 4,766,908 A | 8/1988 | Clement | |
| 4,863,432 A | 9/1989 | Kvalo | |
| 4,950,252 A | 8/1990 | Luther et al. | |
| 4,994,040 A | 2/1991 | Cameron et al. | |
| 5,017,259 A | 5/1991 | Kohsai | |
| 5,040,548 A | 8/1991 | Yock | |
| 5,057,073 A | 10/1991 | Martin | |
| 5,112,312 A | 5/1992 | Luther | |
| 5,115,816 A | 5/1992 | Lee | |
| 5,120,317 A | 6/1992 | Luther | |
| 5,158,544 A | 10/1992 | Weinstein | |
| 5,188,593 A | 2/1993 | Martin | |
| 5,195,962 A | 3/1993 | Martin et al. | |
| 5,207,650 A | 5/1993 | Martin | |
| 5,267,958 A | 12/1993 | Buchbinder et al. | |
| 5,295,970 A | 3/1994 | Clinton et al. | |
| 5,306,247 A | 4/1994 | Pfenninger | |
| 5,322,512 A | 6/1994 | Mohiuddin | |
| 5,328,472 A | 7/1994 | Steinke et al. | |
| 5,350,358 A | 9/1994 | Martin | |
| 5,358,495 A * | 10/1994 | Lynn | A61M 25/0111 604/528 |
| 5,368,567 A | 11/1994 | Lee | |
| 5,378,230 A | 1/1995 | Mahurkar | |
| 5,380,290 A | 1/1995 | Makower et al. | |
| 5,389,087 A | 2/1995 | Miraki | |
| 5,439,449 A | 8/1995 | Mapes et al. | |
| 5,443,457 A | 8/1995 | Ginn et al. | |
| 5,460,185 A | 10/1995 | Johnson et al. | |
| 5,489,271 A | 2/1996 | Andersen | |
| 5,573,520 A | 11/1996 | Schwartz et al. | |
| 5,683,370 A | 11/1997 | Luther et al. | |
| 5,718,678 A | 2/1998 | Fleming, III | |
| 5,772,636 A | 6/1998 | Brimhall et al. | |
| 5,885,251 A | 3/1999 | Luther | |
| 5,919,164 A | 7/1999 | Andersen | |
| 5,947,940 A | 9/1999 | Beisel | |
| 5,957,893 A | 9/1999 | Luther et al. | |
| 5,971,957 A | 10/1999 | Luther et al. | |
| 6,159,198 A | 12/2000 | Gardeski et al. | |
| 6,206,849 B1 | 3/2001 | Martin et al. | |
| 6,228,062 B1 | 5/2001 | Howell et al. | |
| 6,475,187 B1 | 11/2002 | Gerberding | |
| 6,606,515 B1 | 8/2003 | Windheuser et al. | |
| 6,626,869 B1 | 9/2003 | Bint | |
| 6,716,228 B2 | 4/2004 | Tal | |
| 6,726,659 B1 | 4/2004 | Stocking et al. | |
| 6,819,951 B2 | 11/2004 | Patel et al. | |
| 6,821,287 B1 | 11/2004 | Jang | |
| 6,926,692 B2 | 8/2005 | Katoh et al. | |
| 6,962,575 B2 | 11/2005 | Tal | |
| 6,991,625 B1 | 1/2006 | Gately et al. | |
| 6,994,693 B2 | 2/2006 | Tal | |
| 6,999,809 B2 | 2/2006 | Currier et al. | |
| 7,025,746 B2 | 4/2006 | Tal | |
| 7,029,467 B2 | 4/2006 | Currier et al. | |
| 7,037,293 B2 | 5/2006 | Carrillo et al. | |
| 7,074,231 B2 | 7/2006 | Jang | |
| 7,141,050 B2 | 11/2006 | Deal et al. | |
| 7,144,386 B2 | 12/2006 | Korkor et al. | |
| 7,311,697 B2 | 12/2007 | Osborne | |
| 7,364,566 B2 | 4/2008 | Elkins et al. | |
| 7,377,910 B2 | 5/2008 | Katoh et al. | |
| 7,390,323 B2 | 6/2008 | Jang | |
| D600,793 S | 9/2009 | Bierman et al. | |
| D601,242 S | 9/2009 | Bierman et al. | |
| D601,243 S | 9/2009 | Bierman et al. | |
| 7,594,911 B2 | 9/2009 | Powers et al. | |
| 7,691,093 B2 | 4/2010 | Brimhall | |
| 7,722,567 B2 | 5/2010 | Tal | |
| D617,893 S | 6/2010 | Bierman et al. | |
| D624,643 S | 9/2010 | Bierman et al. | |
| 7,819,889 B2 | 10/2010 | Healy et al. | |
| 7,857,788 B2 | 12/2010 | Racz | |
| D630,729 S | 1/2011 | Bierman et al. | |
| 7,909,797 B2 | 3/2011 | Kennedy, II et al. | |
| 7,909,811 B2 | 3/2011 | Agro et al. | |
| 7,922,696 B2 | 4/2011 | Tal et al. | |
| 7,938,820 B2 | 5/2011 | Webster et al. | |
| 7,967,834 B2 | 6/2011 | Tal et al. | |
| 7,976,511 B2 | 7/2011 | Fojtik | |
| 7,985,204 B2 | 7/2011 | Katoh et al. | |
| 8,073,517 B1 | 12/2011 | Burchman | |
| 8,105,286 B2 | 1/2012 | Anderson et al. | |
| 8,192,402 B2 | 6/2012 | Anderson et al. | |
| 8,202,251 B2 | 6/2012 | Bierman et al. | |
| 8,206,356 B2 | 6/2012 | Katoh et al. | |
| 8,361,011 B2 | 1/2013 | Mendels | |
| 8,372,107 B2 | 2/2013 | Tupper | |
| 8,377,006 B2 | 2/2013 | Tal et al. | |
| 8,454,577 B2 | 6/2013 | Joergensen et al. | |
| 8,585,858 B2 | 11/2013 | Kronfeld et al. | |
| 8,657,790 B2 | 2/2014 | Tal et al. | |
| 8,672,888 B2 | 3/2014 | Tal | |
| 8,696,645 B2 | 4/2014 | Tal et al. | |
| 8,784,362 B2 | 7/2014 | Boutilette et al. | |
| 8,827,958 B2 | 9/2014 | Bierman et al. | |
| 8,876,704 B2 | 11/2014 | Golden et al. | |
| 8,882,713 B1 | 11/2014 | Call et al. | |
| 8,900,192 B2 | 12/2014 | Anderson et al. | |
| 8,900,207 B2 | 12/2014 | Uretsky | |
| 8,915,884 B2 | 12/2014 | Tal et al. | |
| 8,956,327 B2 | 2/2015 | Bierman et al. | |
| 9,023,093 B2 | 5/2015 | Pal | |
| 9,126,012 B2 | 9/2015 | Mckinnon et al. | |
| 9,138,252 B2 | 9/2015 | Bierman et al. | |
| 9,180,275 B2 | 11/2015 | Helm | |
| 9,265,920 B2 | 2/2016 | Rundquist et al. | |
| 9,272,121 B2 | 3/2016 | Piccagli | |
| 9,445,734 B2 | 9/2016 | Grunwald | |
| 9,522,254 B2 | 12/2016 | Belson | |
| 9,554,785 B2 | 1/2017 | Walters et al. | |
| 9,566,087 B2 | 2/2017 | Bierman et al. | |
| 9,675,784 B2 | 6/2017 | Belson | |
| 9,713,695 B2 | 7/2017 | Bunch et al. | |
| 9,764,117 B2 | 9/2017 | Bierman et al. | |
| 9,770,573 B2 | 9/2017 | Golden et al. | |
| 9,814,861 B2 | 11/2017 | Boutilette et al. | |
| 9,820,845 B2 | 11/2017 | von Lehe et al. | |
| 9,861,383 B2 | 1/2018 | Clark | |
| 9,872,971 B2 | 1/2018 | Blanchard | |

(56) References Cited

U.S. PATENT DOCUMENTS

| | | |
|---|---|---|
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Fegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 10,926,060 B2 | 2/2021 | Stern et al. |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1* | 6/2004 | Boudreaux ....... A61M 25/0643 604/164.12 |
| 2004/0116901 A1 | 6/2004 | Appling |
| 2004/0167478 A1 | 8/2004 | Mooney |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1* | 2/2008 | Perchik ............ A61M 25/0194 604/96.01 |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1* | 8/2012 | Hall ................. A61M 25/0606 604/164.12 |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tai et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0080939 A1 | 3/2015 | Adams et al. |
| 2015/0094653 A1 | 4/2015 | Pacheco et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Bamell |
| 2016/0114124 A1 | 4/2016 | Tal |
| 2016/0158523 A1 | 6/2016 | Helm |
| 2016/0220786 A1 | 8/2016 | Mitchell et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0239443 A1 | 8/2017 | Abitabilo et al. |
| 2017/0259043 A1* | 9/2017 | Chan ................ A61M 25/1025 |
| 2017/0273713 A1 | 9/2017 | Shah et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1 | 10/2018 | Bierman |
| 2018/0310955 A1 | 11/2018 | Lindekugel et al. |
| 2019/0015646 A1* | 1/2019 | Matlock ................ A61M 29/02 |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 | 7/2019 | Burkholz et al. |

(56) References Cited

U.S. PATENT DOCUMENTS

| | | |
|---|---|---|
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |
| 2022/0323723 A1 | 10/2022 | Spataro et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |

FOREIGN PATENT DOCUMENTS

| | | |
|---|---|---|
| EP | 0730880 A1 | 9/1996 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 00/06221 A1 | 2/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005/096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011/109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014/197614 A2 | 12/2014 |
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016/178974 A1 | 11/2016 |
| WO | 2016/187063 A1 | 11/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/050576 A1 | 3/2019 |
| WO | 2019/146026 A1 | 8/2019 |
| WO | 2019199734 A1 | 10/2019 |
| WO | 2020014149 A1 | 1/2020 |
| WO | 2020069395 A1 | 4/2020 |
| WO | 2020/109448 A1 | 6/2020 |
| WO | 2020/113123 A1 | 6/2020 |
| WO | 2021050302 A1 | 3/2021 |
| WO | 2021/077103 A1 | 4/2021 |
| WO | 2021062023 A1 | 4/2021 |
| WO | 2021081205 A1 | 4/2021 |
| WO | 2021086793 A1 | 5/2021 |
| WO | 2021/236950 A1 | 11/2021 |
| WO | 2022/031618 A1 | 2/2022 |
| WO | 2022/094141 A1 | 5/2022 |
| WO | 2022/133297 A1 | 6/2022 |
| WO | 2022-140406 A1 | 6/2022 |
| WO | 2022/140429 A1 | 6/2022 |
| WO | 2022/217098 A1 | 10/2022 |
| WO | 2023014994 A1 | 2/2023 |
| WO | 2023049498 A1 | 3/2023 |
| WO | 2023049505 A1 | 3/2023 |
| WO | 2023049511 A1 | 3/2023 |

(56) References Cited

FOREIGN PATENT DOCUMENTS

| | | |
|---|---|---|
| WO | 2023049519 A1 | 3/2023 |
| WO | 2023049522 A1 | 3/2023 |

OTHER PUBLICATIONS

PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
PCT/US2020/057397 filed Oct. 26, 2020 International Search Report and Written Opinion dated Mar. 10, 2021.
U.S. Appl. No. 16/398,020, filed Apr. 29, 2019 Non-Final Office Action dated May 11, 2021.
PCT/US2021/039084 filed Jun. 25, 2021 International Search Report and Written Opinion dated Jan. 10, 2022.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
U.S. Appl. No. 16/398,020, filed Apr. 29, 2019 Final Office Action dated Jan. 25, 2022.
U.S. Appl. No. 17/077,728, filed Oct. 22, 2020 Non-Final Office Action dated Feb. 9, 2022.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
U.S. Appl. No. 17/031,478, filed Sep. 24, 2020 Non-Final Office Action dated May 11, 2022.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/014700 filed Jan. 22, 2021 International Search Report and Written Opinion dated Jun. 29, 2021.
PCT/US2021/028018 filed Apr. 19, 2021 International Preliminary Report on Patentability dated Jun. 3, 2022.
POT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
PCT/US2021/064671 filed Dec. 21, 2021 International Search Report and Written Opinion dated May 27, 2022.
POT/US2022/024085 filed Apr. 8, 2022 International Search Report and Wirtten Opinion dated Sep. 12, 2022.
POT/US2022/039614 filed Aug. 5, 2022 International Search Report and Written Opinion dated Dec. 22, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2023/011173 filed Jan. 19, 2023 International Search Report and Written Opinion dated May 22, 2023.
U.S. Appl. No. 17/392,061, filed Apr. 26, 2021 Non-Final Office Action dated Jun. 8, 2023.
U.S. Appl. No. 17/326,017, filed May 20, 2021 Notice of Allowance dated Jul. 3, 2023
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/392,061, filed Aug. 2, 2021 Non-Final Office Action dated Jul. 17, 2023.

* cited by examiner

SPLITABLE CATHETER DOCKING STATION SYSTEM AND METHOD

PRIORITY

This application claims the benefit of priority to U.S. Patent Application No. 62/965,064, filed Jan. 23, 2020, which is incorporated by reference in its entirety into this application.

SUMMARY

Briefly summarized, embodiments disclosed herein are directed to a two-step rapid insertion central catheter ("RICC") system. The two-step RICC system in one embodiment includes an introducer placement system, a docking station and a catheter placement system. The introducer placement system can place an introducer within a vasculature, which can be supported by a docking station that detaches from a distal end of the introducer placement system. The docking station can provide a way to maintain access to the vasculature and allow a clinician to let go of the introducer while it remains in place in the vasculature. In an embodiment, a catheter placement system couples with the docking station and a catheter can be advanced through the introducer into the vasculature. The introducer can then be split and retracted before the catheter placement system disengages the docking station. Finally, the docking station can split and disengage from the catheter. Some embodiments include a guidewire hub to prevent guidewire embolisms, collapsible sterile barriers to prevent contamination, and locking features to prevent premature advancement of guidewires, dilators and the like.

Embodiments described herein provide a simplification of the insertion process for a CVC catheter, or similar device. This requires fewer components, fewer steps to the procedure, and containing the components to be inserted within a sterile barrier, or the like. Embodiments can include a guidewire hub and a locking device that prevents guidewire embolisms, and a docking station that supports the introducer. The docking station allows a clinician to release the introducer during the procedure, which is not possible in current methods where a clinician must maintain a grasp of the introducer while performing additional steps single-handedly.

Disclosed herein is a rapid insertion central catheter system, including an introducer placement system, configured to place an introducer within a vasculature of a patient, having a needle, defining a needle lumen, an introducer guidewire, disposed within the needle lumen, a dilator, defining a dilator lumen, an introducer, supported by an introducer hub, and defining a introducer lumen configured to receive the dilator disposed therein, a guidewire housing including a guidewire advancement assembly coupled to a proximal end of the introducer guidewire, and a needle retraction assembly coupled to a proximal end of the needle, a dilator housing coupled to a distal end of the guidewire housing and including a dilator advancement assembly coupled to a proximal end of a dilator, and a blood flash indicator tube fluidly coupled with the needle lumen. The rapid insertion central catheter system can also include a docking station, releasably coupled to a distal end of the dilator housing, and defining a lumen configured to retain the introducer hub, and a catheter placement system, configured to engage a proximal end of the docking station and place a catheter within a vasculature of a patient, having a docking portion configured to engage the docking station to axially align a catheter with the introducer lumen, a rail, extending proximally from the docking portion, a locking hub, disposed at a proximal end of the rail and defining a locking hub lumen, a catheter guidewire including a guidewire hub permanently attached to a distal end thereof, a portion of the guidewire disposed within the locking hub lumen, a catheter frame, slidably engaged with the rail, and a catheter, supported by the catheter frame.

In some embodiments, the introducer placement system further includes a blood flash actuator, configured to release a vacuum disposed within the blood flash indicator tube to draw a proximal blood flow through the needle lumen and into the blood flash indicator tube. The blood flow disposed within the blood flash indicator tube is observable through the blood flash indicator tube and through the guidewire housing. One of the rail and the catheter guidewire is disposed within a collapsible sterile barrier to prevent contact therewith. The catheter is disposed within the collapsible sterile barrier that includes the rail disposed therein, the catheter frame extending through an aperture a side wall of the sterile barrier and configured to be grasped by a clinician.

In some embodiments, one of the guidewire advancement assembly, the needle retraction assembly, and the dilator advancement assembly includes a release mechanism that requires a pair of finger tabs to move laterally inward prior to allowing any longitudinal movement thereof. The guidewire of the dilator placement system is configured to blunt a tip of the needle when the guidewire is advanced distally through the needle lumen. Distal advancement of the dilator assembly causes the dilator and the introducer to advance distally over the needle and the guidewire. Proximal withdrawal of the needle retraction assembly causes proximal withdrawal of the needle and the introducer guidewire. Distal advancement of the dilator advancement assembly transfers the introducer from the dilator housing to the docking station. Proximal withdrawal of the dilator advancement assembly causes proximal withdrawal of the dilator from the lumen of the introducer.

In some embodiments, the docking station defines a distal surface including an adhesive layer configured to adhere the docking station to a skin surface of a patient. A width of the guidewire hub of the catheter guidewire is greater than a width of the locking hub lumen to prevent a proximal end of the catheter guidewire passing through the locking hub lumen. The docking portion of the catheter placement system includes an introducer retraction assembly configured to split the introducer along a longitudinal axis into a first half and a second half, the first half wound around a first reel and a second half wound around a second reel. The locking hub further includes a guidewire lock, configured to lock the catheter guidewire and prevent longitudinal movement thereof, relative to the locking hub. The docking station includes a breach line extending longitudinally, and is configured to separate along the breach line when a first body portion and a second body portion of the docking station are urged laterally outward.

Also disclosed is a two-step method of placing a catheter within a vasculature of a patient including a first step of placing an introducer using an introducer placement system including a body, a docking station releasably coupled to a distal end of the body, a needle, an introducer guidewire, a dilator, and an introducer, and a second step of placing a catheter using a catheter placement system including a docking portion, a rail including a catheter frame slidably engaged thereto, a catheter releasably coupled to the catheter frame, and a locking hub disposed at a proximal end of the rail, the method including accessing the vasculature using the needle, advancing the introducer guidewire through a lumen of the needle, advancing the dilator, including the introducer disposed thereon, over the needle to transfer the introducer from the body to the docking station, retracting the needle and the guidewire from the dilator, retracting the dilator from the introducer, detaching the body of the introducer placement system from the docking station, coupling the docking portion of the catheter placement system with a proximal end of the docking station, advancing a catheter guidewire distally through a lumen of the catheter and through a lumen of the introducer until a distal portion is disposed distally of a distal tip of the introducer, advancing a catheter frame distally, to advance the catheter through the lumen of the introducer, actuating an introducer retraction assembly to split the introducer along a longitudinal axis into a first half and a second half, winding a first half of the introducer around a first reel and winding a second half of the introducer around a second reel, retracting the catheter guidewire distally from the catheter, removing the catheter placement system from the docking station, and removing the docking station from the catheter.

In some embodiments, accessing the vasculature using the needle further includes actuating a blood flash actuator, configured to release a vacuum disposed within a blood flash indicator tube to draw a proximal blood flow through the needle lumen and into the blood flash indicator tube, to confirm vascular access of the needle. Accessing the vasculature using the needle further includes observing a blood flow through the blood flash indicator tube and through the body of the introducer placement system. One of advancing the introducer guidewire, advancing the dilator, and retracting the needle includes releasing a locking mechanism by pinching a pair of finger tabs together, prior to longitudinal movement of the pair of finger tabs relative to the introducer placement system. Advancing the catheter guidewire distally includes collapsing a guidewire sterile barrier between a guidewire hub and the locking hub of the catheter placement system, the guidewire sterile barrier surrounding the catheter guidewire and preventing a clinician from contacting the catheter guidewire.

In some embodiments, advancing the catheter frame distally includes collapsing a portion of a rail sterile barrier between the catheter frame and a docking portion of the catheter placement system, the rail sterile barrier surrounding the rail and a portion of the catheter to prevent a clinician from contacting the portion of the catheter. A portion of the catheter frame extends through an aperture disposed in a side wall of the rail sterile barrier, and configured to allow a clinician to grasp the portion of the catheter frame to urge the catheter frame distally. Advancing a catheter frame distally includes expanding an extension leg sterile barrier between the locking hub and an extension leg of the catheter, the extension leg sterile barrier surrounding the catheter guidewire and prevents a clinician from contacting the catheter guidewire. Advancing the introducer guidewire through the lumen of the needle further includes blunting a tip of the needle.

In some embodiments, transferring the introducer from the body to the docking station further includes retaining an introducer hub within a lumen of the docking station. Detaching the docking station from the body further includes adhering a distal surface of the docking station to a skin surface of a patient. The catheter guidewire further includes a guidewire hub permanently attached to a proximal end thereof, the guidewire hub configured to prevent the proximal end of the catheter guidewire entering the lumen of the catheter. Coupling the catheter placement system with the proximal end of the docking station further includes coupling a clamp of the introducer retraction assembly with an introducer hub, the clamp opening a valve disposed within the introducer hub. Advancing the catheter guidewire proximally further includes unlocking a guidewire lock to allow longitudinal movement of the catheter guidewire relative to the catheter placement system, followed by locking the guidewire lock, to inhibit longitudinal movement of the catheter guidewire relative to the catheter placement system when a distal tip of the catheter guidewire is disposed proximate a target location.

In some embodiments, actuating an introducer retraction assembly further includes rotating a twist knob of the introducer retraction assembly. Removing the catheter placement system from the docking station further includes removing a cap portion of the catheter placement system to allow transverse movement of the catheter placement system relative to the catheter. Removing the docking station from the catheter further includes splitting the docking station longitudinally along a breach line by urging a first portion and a second portion laterally outward.

Also disclosed is a rapid insertion central catheter system, including an introducer placement system, configured to place an introducer within a vasculature of a patient, a docking station, releasably coupled to a distal end of the introducer placement system, and a catheter placement system, configured to engage a proximal end of the docking station and place a catheter within a vasculature of a patient.

In some embodiments, the introducer placement system includes one of a needle, an introducer guidewire, a dilator, an introducer, an introducer hub, and a blood flash indicator tube. The introducer placement system further includes a blood flash actuator configured to release a vacuum disposed within the blood flash indicator tube to draw a proximal blood flow through a lumen of the needle and into the blood flash indicator tube. The catheter placement system includes one of a docking portion, a rail, a locking hub, a catheter guidewire, and a catheter frame. One of the rail, the catheter, and the catheter guidewire is disposed within a collapsible sterile barrier to prevent contact therewith. The introducer placement system includes one of a guidewire advancement assembly, a needle retraction assembly, and a dilator advancement assembly. One of the guidewire advancement assembly, the needle retraction assembly, and the dilator advancement assembly includes a release mechanism.

Also disclosed is a method of placing a catheter within a vasculature of a patient, including, placing an introducer within the vasculature of the patient using an introducer placement system including a body and a docking station, detaching the body of the introducer placement system from the docking station, coupling a catheter placement system with the docking station, advancing a catheter into the vasculature of the patient, removing the introducer using an introducer retraction assembly, and removing the catheter placement system and the docking station.

In some embodiments, placing the introducer further includes transferring the introducer from the body of the introducer placement system to the docking station. The method further includes retaining an introducer hub of the introducer within a lumen of the docking station. The method further includes actuating a blood flash actuator, configured to release a vacuum disposed within a blood flash indicator tube to draw a proximal blood flow through a needle lumen and into the blood flash indicator tube, to confirm vascular access of a needle.

In some embodiments, placing an introducer within the vasculature of the patient further includes advancing an introducer guidewire through the needle lumen and blunting a tip of the needle. Advancing the catheter into the vasculature of the patient further includes a guidewire hub permanently attached to a proximal end of a catheter guidewire, the guidewire hub configured to prevent a proximal end of the catheter guidewire entering a lumen of the catheter. Removing the introducer further includes splitting the introducer along a longitudinal axis.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
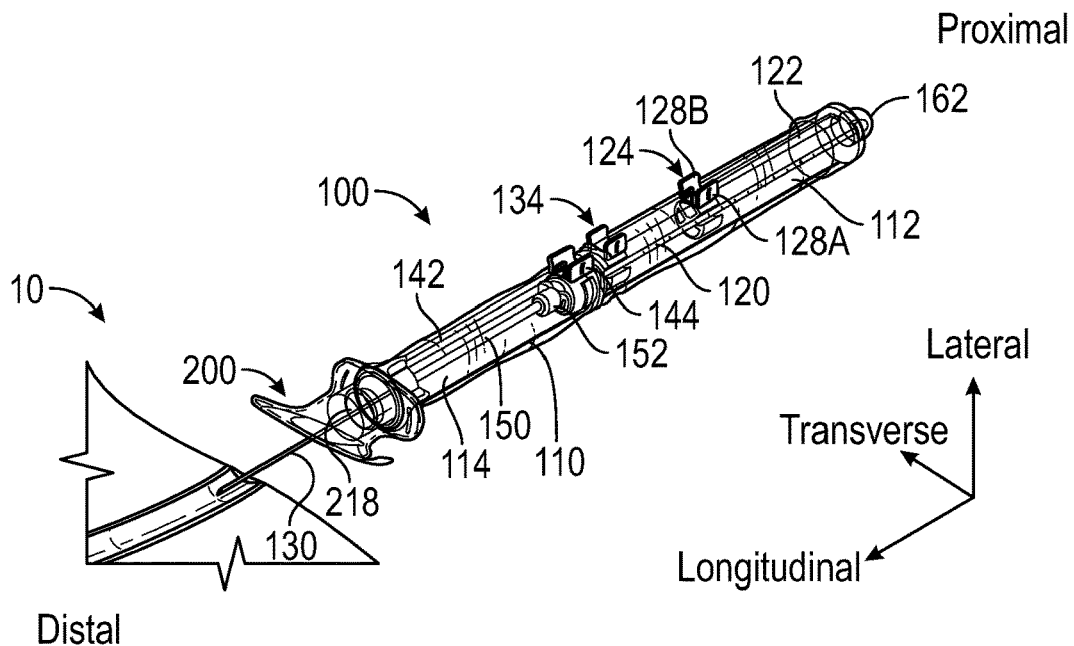
FIGS. 1A-1C show a perspective view of a two-step rapid insertion catheter system including an introducer placement system, a docking station, and a catheter placement system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, as shown in FIG. 1A, a longitudinal axis extends substantially parallel to an axial length of a needle 130. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

Figure 1B:
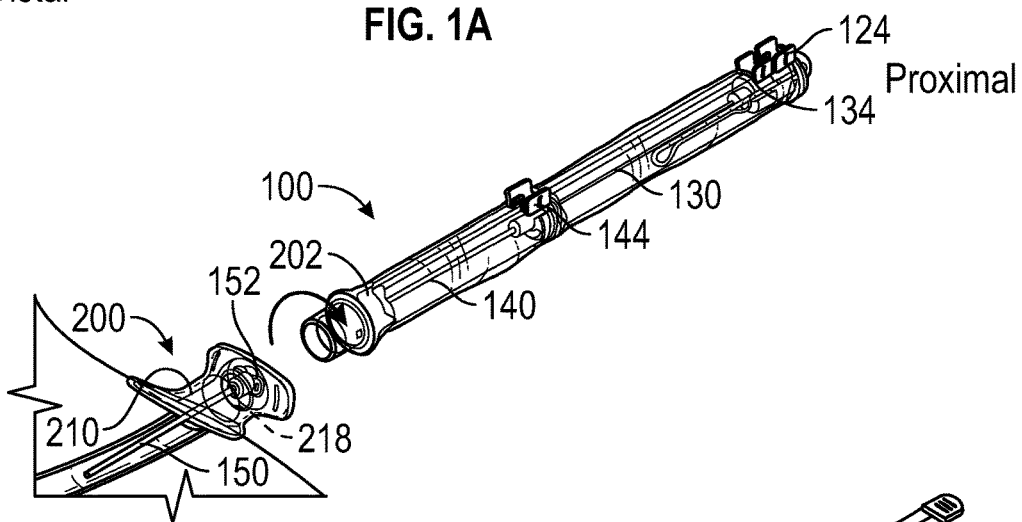
Figure 1C:
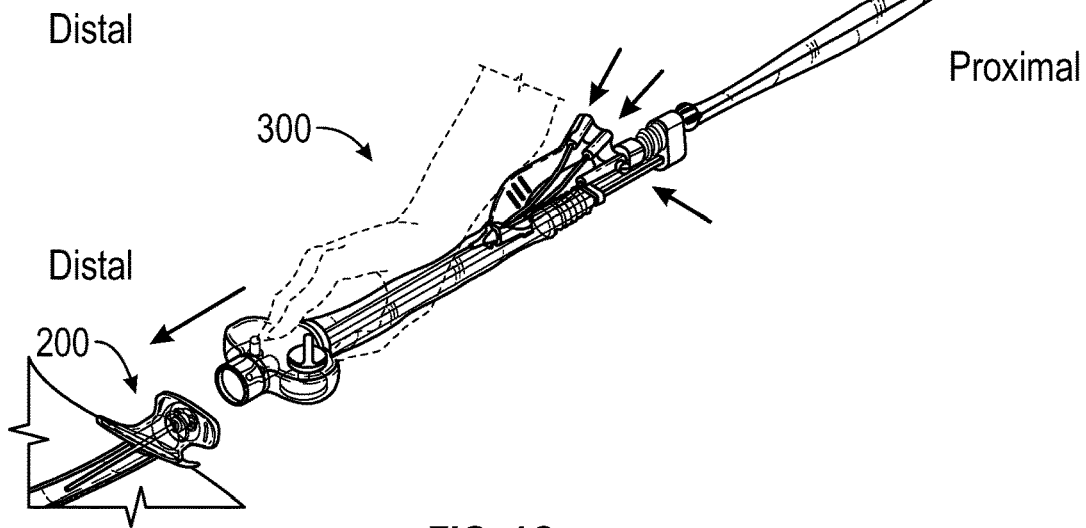
Figure 2A:
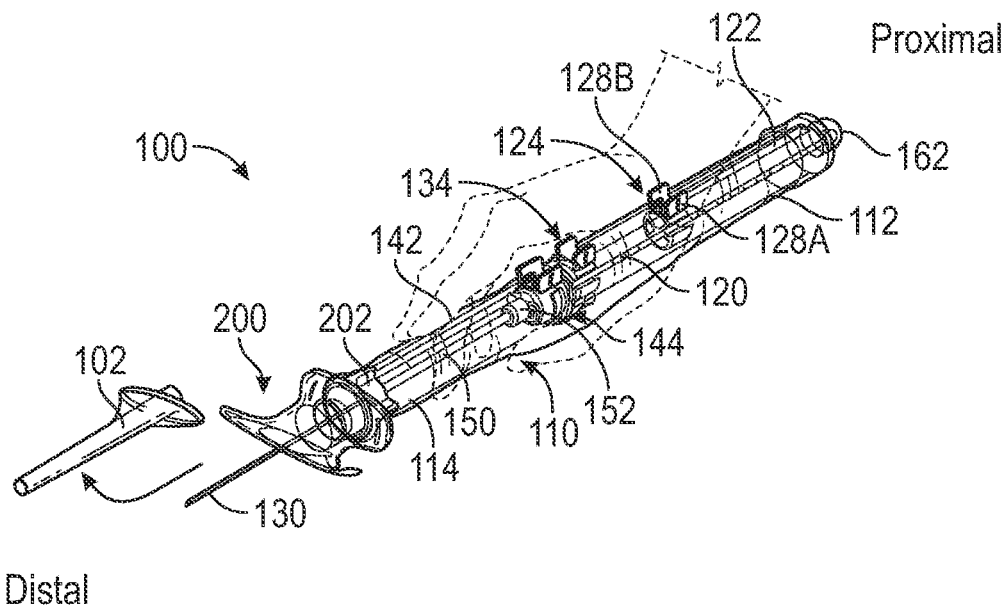
FIGS. 2A-2E show various details of the introducer placement system of FIGS. 1A-B, in accordance with embodiments disclosed herein.
Figure 2B:
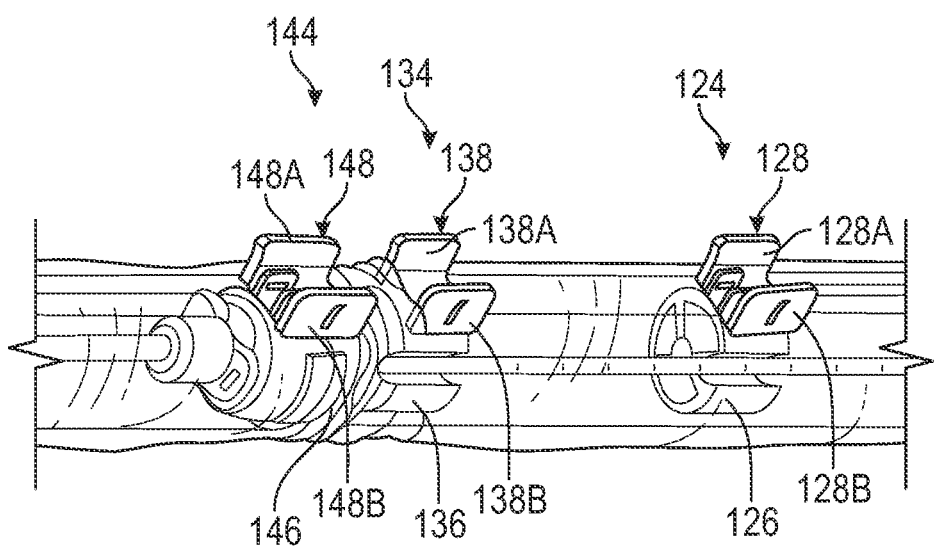

FIGS. 1A-1C show various details of a two-step rapid insertion central catheter ("RICC") system 10, including an introducer placement system 100, a docking station 200, and a catheter placement system 300, in accordance with embodiments described herein. FIGS. 2A-2E show further details of the introducer placement system 100 and the docking station 200. FIGS. 3A-3B show further details of the catheter placement system 300 and the docking station 200. While embodiments disclosed herein are directed to placing a central venous catheter (CVC), it will be appreciated that this is exemplary and the systems and methods disclosed herein can be used to place various elongate medical devices, including without limitation, peripherally inserted central catheters (PICC), dialysis catheters, midline catheters, peripheral catheters, or the like.

The introducer placement system 100 includes a substantially cylindrical body 110 extending from a proximal end to a distal end and defining a substantially circular cross-section. Although it will be appreciated that other cross-sectional shapes are also contemplated. In an embodiment, the body 110 is formed of a translucent material, which advantageously allows a clinician to observe components disposed therein, as will be discussed in more detail herein.

A proximal portion of the body 110 includes a guidewire housing 112 and a distal portion of the body 110 includes a dilator housing 114.

The guidewire housing 112 includes an elongate slot 122 disposed in an upper surface of the guidewire housing 112. The slot 122 extends longitudinally and communicates with an interior of the guidewire housing 112. The guidewire housing 112 includes a guidewire advancement assembly 124 that comprises a guidewire carriage 126, disposed within an interior of the guidewire housing 112, and a guidewire finger tab 128 that extends through the slot 122 to an exterior of the guidewire housing 112. In an embodiment, the guidewire finger tab 128 includes a release mechanism, which requires the clinician to actuate in order to allow the guidewire advancement assembly 124 to slide longitudinally. For example, as shown in FIG. 2B, the guidewire advancement assembly 124 can include a first finger tab 128A and a second finger tab 128B that require the clinician to pinch the finger tabs 128A, 128B laterally inwards before the guidewire advancement assembly 124 is allowed to slide longitudinally. In an embodiment, the guidewire finger tab 128 includes an actuator button that must be depressed before the guidewire advancement assembly 124 can slid longitudinally.

The guidewire carriage 126 is configured to be slidabley engaged with an interior of the guidewire housing 112. For example, the guidewire carriage 126 defines a substantially cylindrical shape extending longitudinally, and defining a substantially circular cross-sectional shape that is slidabley engaged with a cylindrical interior of the guidewire housing 112. In an embodiment, the guidewire carriage 126 can further include various apertures and notches so as to accommodate various additional structures disposed within guidewire housing 112, such as blood flash tubes, or the like, as will be described in more detail herein. The guidewire carriage 126 is coupled with a proximal end of an introducer guidewire 120 that is disposed axially within the guidewire housing 112. The introducer guidewire 120 extends distally from the guidewire carriage 126 to a distal end of the body 110.

The guidewire housing 112 further includes a needle advancement assembly 134 that comprises of a needle carriage 136, disposed within an interior of the guidewire housing 112, and a needle finger tab 138 that extends through the slot 122 to an exterior of the guidewire housing 112. In an embodiment, the needle finger tab 138 includes a release mechanism, e.g. finger tabs 138A, 138B, which requires the clinician to actuate in order to allow the needle advancement assembly 134 to slide longitudinally, as described herein. The needle carriage 136 is configured to be slidabley engaged with an interior of the guidewire housing 112. For example, the needle carriage 136 defines a substantially cylindrical shape extending longitudinally, and defining a substantially circular cross-sectional shape that is slidabley engaged with a cylindrical interior of the guidewire housing 112. In an embodiment, the needle carriage 136 further includes various apertures and notches so as to accommodate various additional structures disposed within guidewire housing 112, such as blood flash tubes, or the like, as will be described in more detail herein. The needle carriage 136 is coupled with a proximal end of a needle 130 that is disposed axially within the body 110. The needle 130 defines a needle lumen 132 and extends distally from the needle carriage 136 to a point distal of the distal end of the body 110.

The guidewire housing 112 further includes a blood flash tube 160 that is coupled to the needle carriage 136 and is in fluid communication with the needle lumen 132. The blood flash tube 160 extends along an interior surface of the guidewire housing 112, between the needle carriage 136 and a proximal end of the guidewire housing 112. The blood flash tube 160 is made of a translucent material, which together with the translucent material of the guidewire housing 112, allows a clinician to observe a blood flow within the blood flash tube 160 to confirm a distal tip of the needle has accessed a vasculature of a patient.

In an embodiment, the blood flash tube 160 is coupled with an actuator 162, e.g. a blood flash button. The blood flash tube 160 is evacuated so as to provide a vacuum disposed therein. As the needle is inserted into the patient, a clinician can depress the actuator 162 that in turn provides fluid communication between the blood flash tube 160 and the needle lumen 132. The vacuum within the blood flash tube 160 draws a blood flow proximally through the needle lumen 132 and into the blood flash tube 160 to facilitate observation of the blood flow within the blood flash tube 160, confirming the needle tip has access the vasculature. Advantageously, the vacuum draws a blood flow faster than would otherwise be drawn, providing faster venous access results and preventing the needle from being advanced further into an incorrect vessel, e.g. an artery, or prevents over insertion of the needle 130, thereby breaching a far wall of the vessel. Either of which can be detrimental to the patient.

The dilator housing 114 includes an elongate slot 142 disposed in an upper surface of the dilator housing 114. The slot 142 extends longitudinally and communicates with an interior of the dilator housing 114. The dilator housing 114 includes a dilator advancement assembly 144 that comprises a dilator carriage 146, disposed within an interior of the dilator housing 114, and a dilator finger tab 148 that extends through the dilator housing slot 142 to an exterior of the dilator housing 114. In an embodiment, the dilator finger tab 148 includes a release mechanism, e.g. finger tabs 148A, 148B, which requires the clinician to actuate in order to allow the dilator advancement assembly 144 to slide longitudinally, as described herein.

The dilator carriage 146 is configured to be slidabley engaged with an interior of the dilator housing 114. For example, the dilator carriage 146 defines a substantially cylindrical shape extending longitudinally, and defining a substantially circular cross-sectional shape that is slidabley engaged with a cylindrical interior of the dilator housing 114. In an embodiment, the dilator carriage 146 further includes various apertures and notches so as to accommodate various additional structures disposed within the dilator housing 114, as described herein.

Figure 2C:
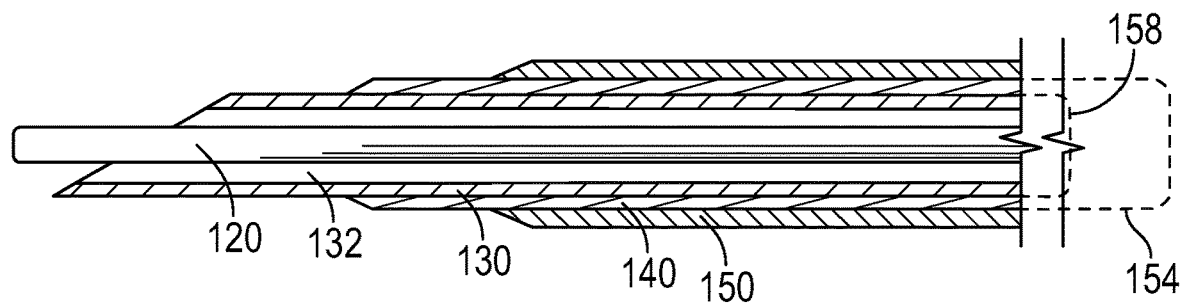
Figure 3A:
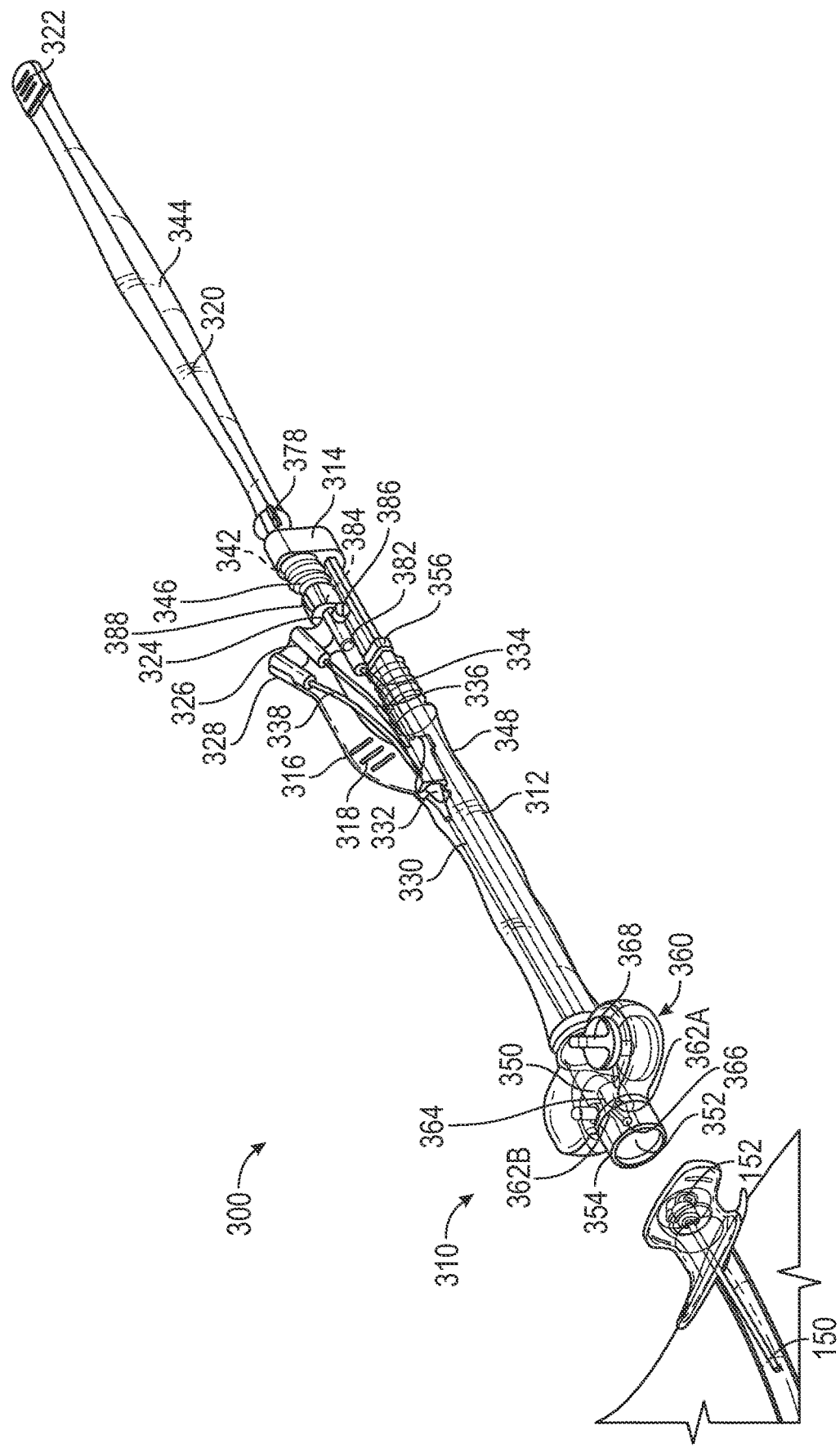
FIGS. 3A-3C show various details of the catheter placement system of FIG. 1C, in accordance with embodiments disclosed herein.
Figure 3B:
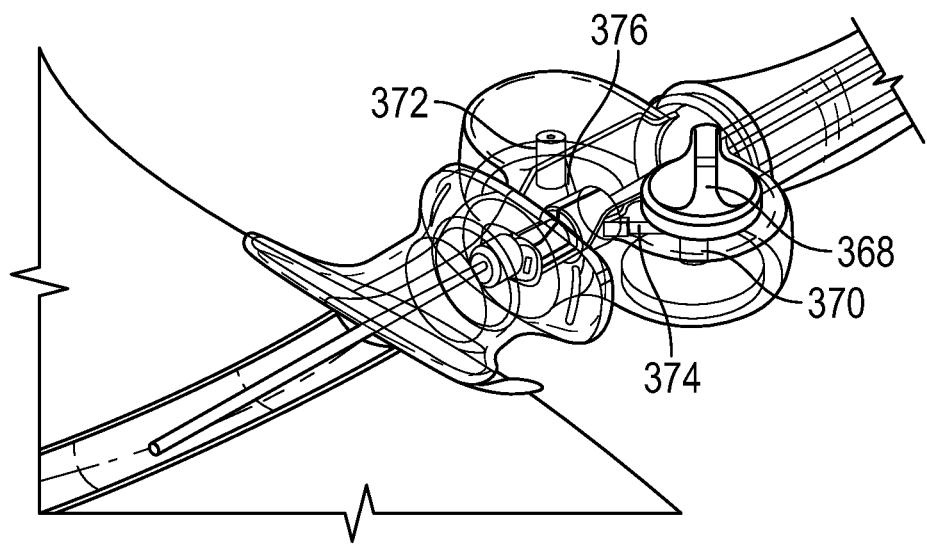

The dilator carriage 146 is coupled with a proximal end of a dilator 140, which is disposed axially within the dilator housing 114, and defines a dilator lumen 158, as shown in FIG. 2C. The dilator 140 extends distally from dilator carriage 146 to a distal end of the body 110. A splittable introducer sheath ("introducer") 150 is axially disposed on an outer surface of the dilator 140 and is supported by an introducer hub 152. The introducer 150 defining an introducer lumen 154. The dilator 140 supports the introducer 150 and facilitates insertion thereof prior to being retracted, as will be discussed in more detail herein.

A docking station 200 is releasably coupled to a distal end of the body 110, for example, a distal end of dilator housing 114. In an embodiment, a spin nut 202 releasably secures the docking station to a distal end of the body 110, although other suitable attachment mechanisms, such as lugs, interference fit, luer lock, clips, protrusion and detents, combinations thereof, or the like, are contemplated.

Figure 2D:
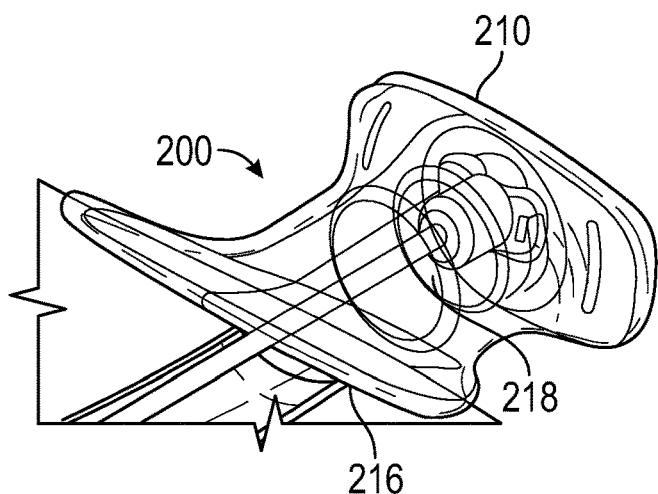
Figure 2E:
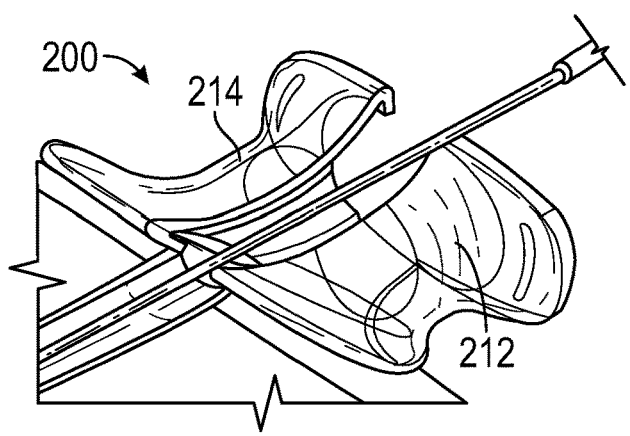

As shown in FIGS. 2D-2E, the docking station 200 includes a body 210 that is formed of a first body portion 212 and a second body portion 214 that engage along a longitudinal axis to define the docking station body 210. In an embodiment, the first body portion 212 and the second body portion 214 engage along a longitudinally vertical plane, although it will be appreciated the first body portion 212 and the second body portion 214 can engage along longitudinally horizontal planes, or planes of other orientations, and fall within the scope of the present invention. In an embodiment, the first body portion 212 and the second body portion 214 are separable by urging the body portions 212, 214 apart, perpendicular to the longitudinal axis. This facilitates removal of the docking station from the insertion site once the catheter has been placed, as will be described in more detail herein.

The docking station body 210 defines a lumen 218 extending longitudinally and is configured to receive one of a distal portion of the dilator housing 114, a needle 130, a dilator 140, an introducer 150, or an introducer hub 152, or combinations thereof. In an embodiment, the lumen 218 is configured to retain the introducer hub 152 therein. Advantageously, this allows a clinician to release the introducer 150 during the procedure and still maintain vascular access therethrough. The docking station 200 maintains the introducer 150 at an accessible angle and can align additional structures with the introducer lumen 154 for introduction into the vasculature, as described herein.

The docking station body 210 includes a distal surface 216 configured to engage a skin surface of the patient and, in an embodiment, includes an adhesive layer disposed thereon. The distal surface 216 provides an increased surface area to improve adhesion between the docking station 200 and the skin surface of the patient, providing increased stabilization. Further, the distal surface 216 can be angled relative to the longitudinal axis to stabilize the lumen of the docking station 200 at a preferred insertion angle. In an embodiment, the distal surface 216 can further include various other layers that include various anti-microbial, anti-bacterial, hemostatic properties, combinations thereof, or the like. The docking station 200 further includes a concave side surface configured to provide a comfortable gripping surface for a clinician. The concave shape directs a clinician's fingers to grasp a mid-point of the side surfaces of the docking station 200.

Figure 3C:
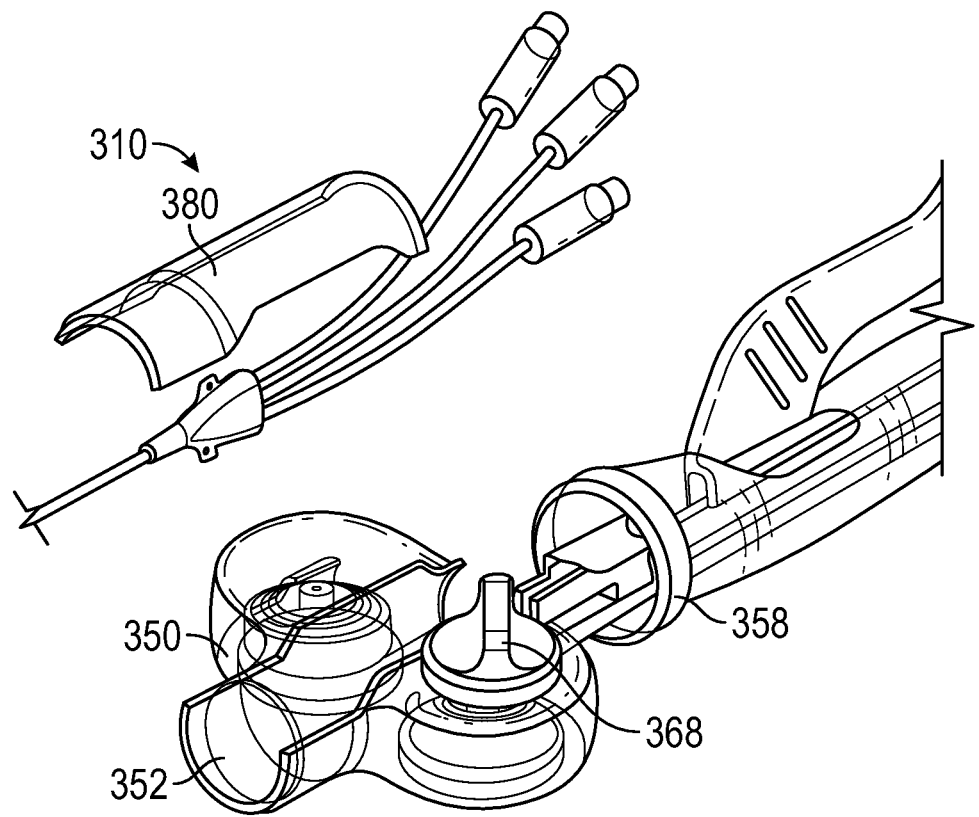

As shown in FIGS. 3A-3C, a catheter placement system 300 includes a docking portion 310 disposed at a distal end, a rail 312 extending proximally from a proximal side of the docking portion 310 and a locking hub 314 disposed at a distal end of the rail 312, the locking hub 314 defining a locking hub lumen 342 extending along a longitudinal axis. The rail 312 extends along a longitudinal axis, from a lower edge of the docking portion 310 so as to axially align the catheter 330 with a central lumen 352 of the docking portion 310. A distal end of the docking portion 310 includes a connector 354 configured to engage a proximal end of the docking station 200 and axially align the central lumen 352 of the docking portion 310 with the central lumen 218 of the docking station 200. In an embodiment, the connector 354 can be a male luer lock that engages a female luer lock disposed at a proximal end of the docking station. It will be appreciated that other engagement structures are also contemplated including mechanical fit, interference fit, snap fit, press fit, spin nut, clips, protrusions and detents, combinations thereof and the like.

A catheter frame 316 is slidabley engaged with an upper surface of the rail 312 and extends transversely upwards and proximally to define a handle 318. A distal portion of the catheter frame 316 is configured to retain a portion of a catheter 330, for example a catheter hub 332 is held by the catheter frame 316 in an interference fit. A proximal portion of the catheter frame 316 includes one or more clips, each of which are configured to retain a proximal end of an extension leg that extends from a proximal end of the hub 332. For example, as shown in FIG. 3A, the catheter hub 332 includes a first extension leg 334, a second extension leg 336, and a third extension leg 338. The catheter frame 316 includes a first clip 324, second clip 326 and third clip 328 that are configured to retain a first extension leg 334, a second extension leg 336, and a third extension leg 338 respectively. The clips 324, 326, 328 can retain the extension legs 334, 336, 338 and convenient angles to access the extension legs, for example to flush the lumens of the catheter with saline prior to placement.

In an embodiment, the first clip 324 aligns a first extension leg 334 with a locking hub lumen 342 and is configured to receive a catheter guidewire 320. The first extension leg 334 can further include a flushing manifold 382 that includes one or more valves, a guidewire port 384, and allows a lumen of the catheter to be flushed with saline prior to placement, but prevents proximal flow thereof. A catheter guidewire 320 extends through the locking hub lumen 342 and is aligned with a lumen of the first extension leg 334. In an embodiment, the first extension leg 334 further includes a spin nut 388 or similar connector that couples the catheter 330, and catheter frame 316 coupled thereto, to a distal side of the locking hub 314 and prevents the catheter frame 316 from sliding longitudinally, relative to the rail 312. In an embodiment, the spin nut 388 further includes a sterile barrier, e.g. extension leg sterile barrier 348 disposed between the spin nut 388 and the locking hub 314 as discussed in more detail herein.

The locking hub 314 further includes a guidewire lock 378, for example a collet lock that can be twisted to secure the catheter guidewire 320 in place, relative to the locking hub 314 and twisted in the opposite direction to allow the catheter guidewire 320 to slid relative to the locking hub 314. The catheter guidewire 320 includes a guidewire hub 322 permanently attached to a proximal end thereof. The guidewire hub 322 is configured to prevent a proximal end of the catheter guidewire 320 from advancing through the locking hub lumen 342. Advantageously, the guidewire lock 378 allows a clinician to lock the catheter guidewire 320 in place and let go of the catheter guidewire 320 to carry out other procedures. This contrasts with current systems that require a clinician to maintain a grasp of the guidewire to prevent the guidewire being drawn into a vasculature of the patient, causing an embolism and various associated complications. Further, the guidewire hub 322 is configured to prevent the proximal end of the catheter guidewire 320 from advancing through the locking hub lumen 342 and into a lumen of the catheter 330 such that if a clinician releases the catheter guidewire 320 without the guidewire lock 378 secured, the catheter guidewire 320 still cannot be drawn into the vasculature of the patient. This contrasts with current systems and methods that require devices to be withdrawn over a proximal end of the guidewire.

The catheter guidewire 320 further includes a sterile barrier 344 encircling the catheter guidewire 320 and extending from the guidewire hub 322 to the locking hub 314. The sterile barrier can include a gas impermeable film, such as polyethylene, polypropylene, or the like, to maintain the catheter guidewire 320 in a sterile environment and prevents a clinician from contacting a portion of the catheter guidewire 320 that is to be advanced into a vasculature of the patient. Further, the barrier 344 prevents exposure of body fluids to the clinician when the catheter guidewire 320 is withdrawn from the vasculature. In an embodiment, the barrier 344 is collapsible to allow the catheter guidewire 320 to be advanced distally.

The catheter placement system 300 also includes a sterile barrier 346 extending between the locking hub 314 and the first extension leg 334, to maintain the catheter guidewire 320 within a sterile environment as it extends between the locking hub 314 and the first extension leg 334. The catheter placement system 300 also includes a rail sterile barrier 348 extending between the locking hub 314 and the proximal end of the docking portion 310. The rail sterile barrier 348 encircles the rail 312 and a portion of the catheter 330. Advantageously, the rail sterile barrier 348 maintains the catheter 330 in a sterile environment and prevents a clinician from contacting a portion of the catheter 330 that is to be advanced into a vasculature of the patient. Further, the barrier 348 prevents exposure of body fluids to the clinician when the catheter 330 is withdrawn from the vasculature. In an embodiment, the rail barrier 348 includes an opening through which one of the catheter frame 316, one or more extension legs 334, 336, 338, the catheter hub 332, or combinations thereof can extend. In an embodiment, a proximal end of the rail barrier 348 is coupled to a slide ring 356 that is slidable engaged with the rail 312 and allows a proximal end of the rail barrier 348 to slide longitudinally. In an embodiment, a distal end of the rail barrier 348 is coupled to a collar 358 that is coupled to a proximal end of the docking portion 310.

The docking portion 310 includes a housing 350 that defines a central lumen 352 extending therethrough. As shown in FIG. 3C, the housing 350 includes a cap 380 that extends over a portion of the central lumen 352 of the housing. The cap 380 is separable from the housing 350 to allow the catheter 330 to be released from the docking portion 310 once the catheter is placed intravenously, as will be described in more detail herein.

The docking portion 310 further includes an introducer retraction assembly 360 that includes a clamp 362 configured to engage an introducer hub 152. The clamp 362 defines a clamp lumen 366 that allows the clamp 362 to engage the dilator and allow various elongate medical devices to pass therethrough. For example, the catheter 330 can pass through the clamp 362 and into a lumen of the introducer 150. In an embodiment, the clamp 362 opens a valve disposed within the introducer hub 152. The valve configured to prevent proximal blood flow when the docking station 200 is detached from the introducer placement system 100. The clamp 362 opens the valve when the catheter placement system 300 is connected to provide a pathway for the catheter 330 to pass through. The clamp 362 further includes a breach line 364 extending longitudinally and configured to facilitate separation of the clamp 362 into a first half 362A and a second half 362B. The breach line 364 can include a scoreline, perforation, laser cut line, or similar line of weakness to facilitate separation of the clamp 362 into a first half 362A and a second half 362B.

The introducer retraction assembly 360 further includes a first reel 370 and a second reel 372 disposed within the housing 350 and laterally spaced apart so as to be disposed on opposite sides of a central axis of the housing 350. In an embodiment, the first reel 370 and the second reel 372 are coupled by means of a gear mechanism such that as first reel 370 is turned, the gear mechanism causes the second reel 372 to also turn. Similarly, it will be appreciated that as the second reel 372 is turned the gear mechanism causes the first reel 370 to also turn. In an embodiment, as the first reel 370 is turned, e.g. in a clockwise direction, the gear mechanism causes the second reel 372 to turn in an opposite direction, e.g. in an anti-clockwise direction.

The first reel 370 includes a first pull tab 374 that extends between the first reel 370 and the first half of the clamp 362A. The second reel 372 includes a second pull tab 376 that extends between the second reel 372 and the second half of the clamp 362B. A twist knob 368 is coupled to the first reel 370 to allow a clinician to turn the first reel 370 and the second reel 372, this in turn retracts the first pull tab 374 about the first reel 370 and the second pull tab 376 about the second reel 372 that separates the clamp 362, the introducer hub 152, and the introducer 150 coupled there to, along the longitudinal axis, into two separate halves and winds each half about the respective first and second reels 370, 372. In an embodiment, the second reel 372 is coupled to a second twist knob (not shown) and the first reel 370 and the second reel 372 are configured to rotate independently of each other. It will be appreciated that other mechanisms and methods of turning the reels 370, 372 are also contemplated to fall within the scope of the present invention.

Method of Use

In an exemplary method of use a Rapid Insertion Central Catheter (RICC) system 10 is provided including an introducer placement system 100, a docking station 200, and a catheter placement system 300. Generally, the method includes a two-step process of using the introducer placement system 100 to place the docking station 200 and an introducer 150 within a vasculature of a patient, followed by the removal of the introducer placement system 100 from the docking station 200 and the coupling of a catheter placement system 300 to the docking station 200 for the placement of a catheter 330.

Figure 4A:
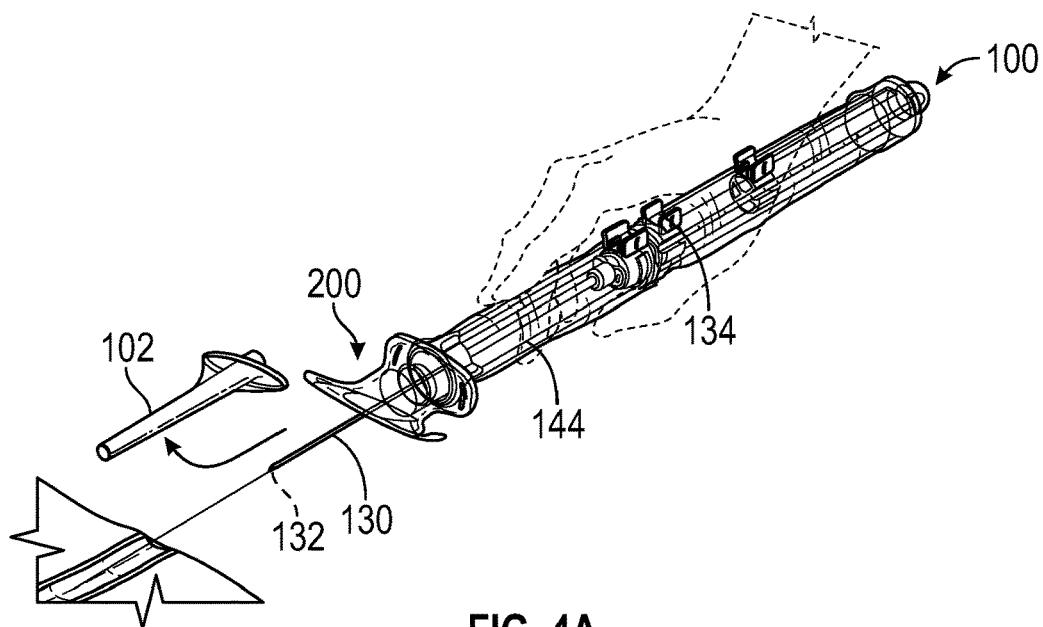
FIGS. 4A-4G show various stages of placing an introducer using the introducer placement system of FIG. 1A-1B, in accordance with embodiments disclosed herein.

As shown in FIG. 4A, an introducer placement system 100 is provided including a docking station 200 releasably coupled to a distal end thereof, as described herein. The introducer placement system 100 includes a needle 130, coupled to a needle advancement assembly 134, and extending distally, through a lumen 218 of the docking station 200 to a point that is distal to a distal surface 216 of the docking station. The introducer placement system 100 and docking station 200 assembly further includes a cap 102 disposed over a distal portion of the needle 130 and engages with a distal surface 216 of the docking station 200, a distal end of the docking station lumen 218, or combinations thereof. The cap 102 is formed of a resilient material and is configured to protect the needle from damage during transport, prevent accidental needle stick injuries and provide a sterile barrier to prevent contamination of the needle 130 prior to use. As such, the cap 102 is removed and the introducer placement system 100 and docking station 200 assembly is ready for use.

Figure 4B:
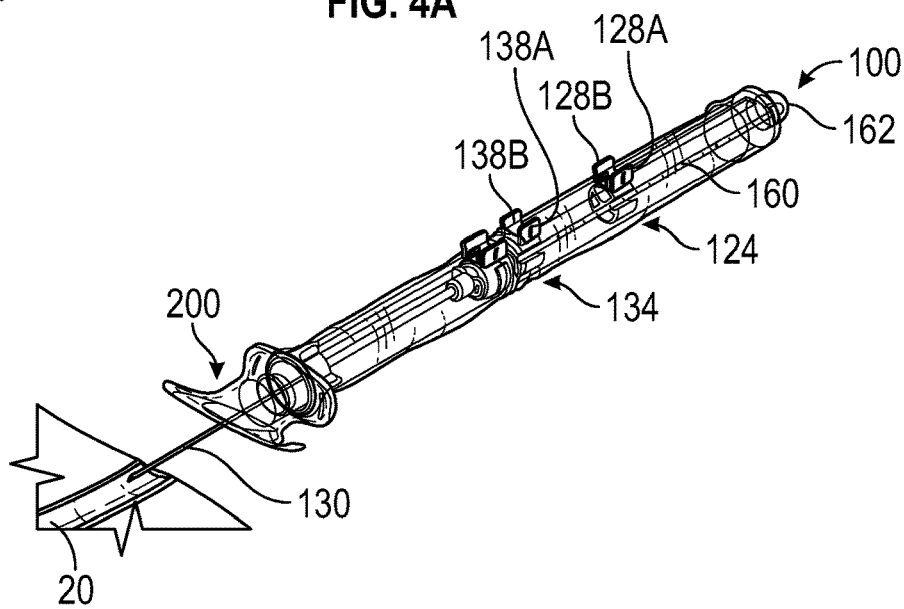

The introducer placement system 100 and docking station 200 assembly is advanced distally until a distal tip of the needle 130 penetrates a skin surface of the patient. The clinician then actuates the blood flash button 162 which releases the vacuum within the blood flash tube 160. As shown in FIG. 4B, the needle 130 is advanced until a tip accesses a vasculature 20 of the patient. The vacuum, released by the blood flash button 162, induces a proximal flow through the needle lumen 132 and into the blood flash tube 160, which is in fluid communication with the needle lumen 132. The clinician can observe a blood color and a presence/absence of a pulsatile blood flow through the blood flash tube 160 to determine if the needle 130 has accessed a venous or arterial vasculature.

Figure 4C:
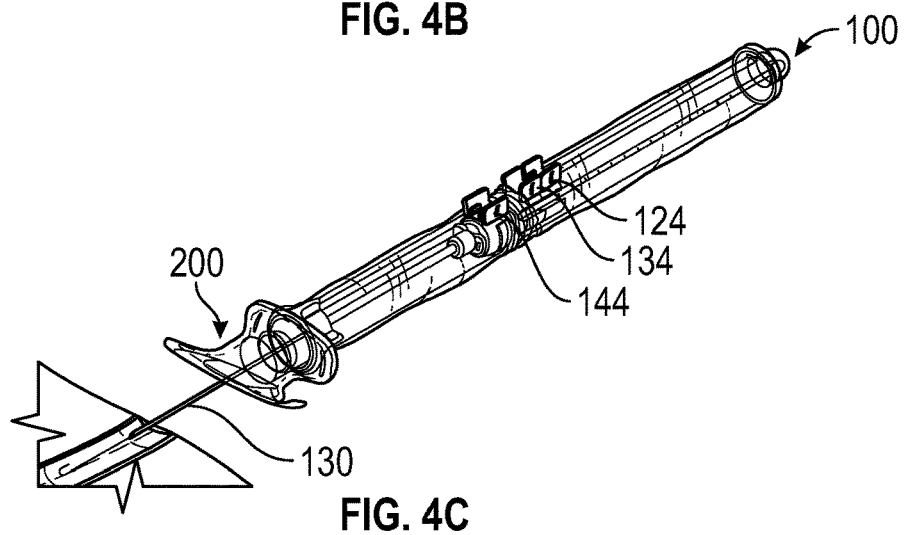

As shown in FIG. 4C, once correct vasculature access has been confirmed, the guidewire advancement assembly 124 can be actuated to advance a distal portion of the introducer guidewire 120 through the needle lumen 132 and into the vasculature 20 of the patient. To actuate the guidewire advancement assembly 124 a clinician can urge the finger tab of the guidewire assembly, which is coupled with the guidewire carriage 126, in a distal direction. In an embodiment, the guidewire finger tab 128 includes a locking mechanism, as described herein, which requires a clinician to pinch a pair of finger tabs 128A, 128B laterally inward to allow the guidewire advancement assembly 124 to advance distally. As the distal portion of the introducer guidewire 120 advances past the tip of the needle 130, the guidewire abrades the edges of the needle 130 causing the needle to blunt. Advantageously, this prevents accidental needle stick injuries when the needle is removed from the vasculature 20.

Figure 4D:
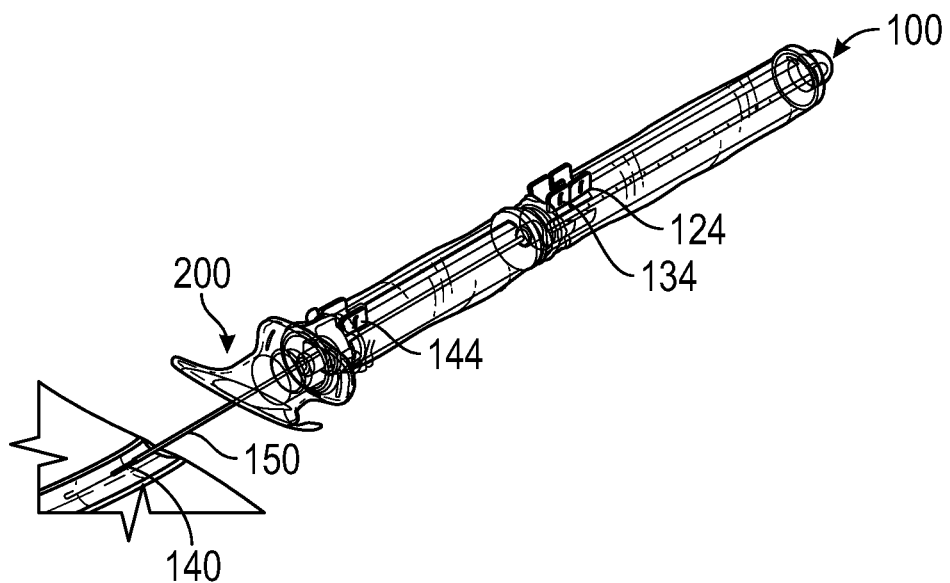

As shown in FIG. 4D, the dilator advancement assembly 144 is then advanced distally to advance a dilator 140, and an introducer 150 disposed thereon. The dilator advancement assembly 144 is advanced by actuating the dilator finger tab 148 in a distal direction. In an embodiment, the dilator finger tab 148 can include a locking mechanism that requires a pair of tabs to be pinched laterally inward before the dilator advancement assembly 144 can be advanced distally, as described herein. The dilator advancement assembly 144 is advanced until an introducer hub 152, which supports the introducer 150, is disposed within a lumen 218 of the docking station 200. In an embodiment, a portion of the docking station lumen 218 is shaped to match an outer surface of the introducer hub 152, such that the introducer hub 152 is retained by the docking station in a friction fit engagement. It will be appreciated that the docking station lumen 218 can further include various clips, detents, protrusions, barbs, combinations thereof, and the like, to further retain the introducer hub 152 within the lumen 218.

As shown in FIG. 2C the dilator 140 includes a tapered tip that fits snugly about an outer surface of the needle 130. Further, an introducer 150 also includes a tapered tip that fits snugly about an outer surface of the dilator 140. Accordingly, as the dilator advancement assembly 144 is advanced, the dilator 140 dilates the insertion site. Further the introducer 150 dilates the insertion site yet further. This dilates the insertion site from the diameter of the needle 130 to a diameter sufficient to receive the catheter 330, e.g. a triple lumen central venous catheter.

Figure 4E:
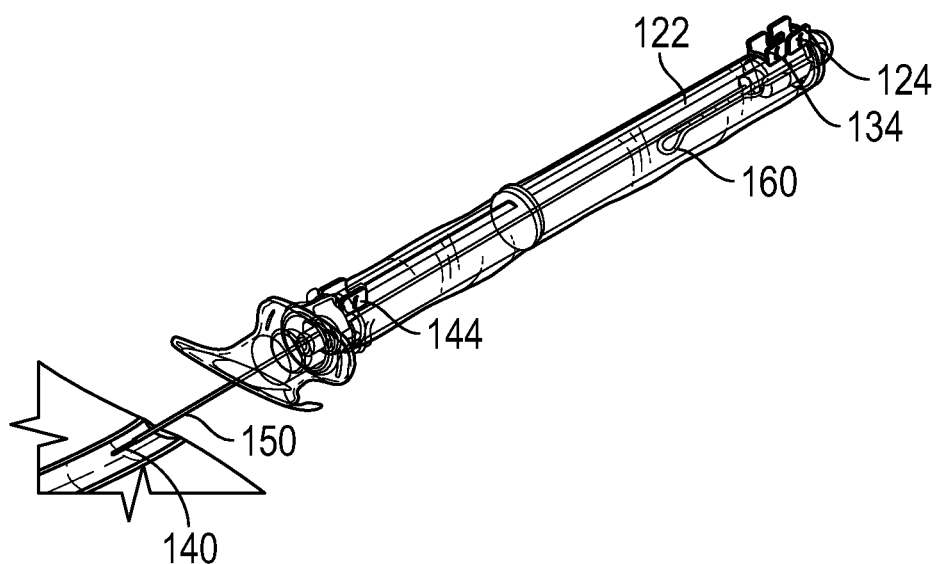

As shown in FIG. 4E, once a distal portion of the introducer is disposed within the vasculature 20 of the patient, the needle advancement assembly 134 can be actuated to retract the needle 130 proximally leaving the dilator 140 and the introducer 150 in place. To note, both the needle advancement assembly 134 and the guidewire advancement assembly 124 are slidably engaged with the guidewire housing slot 122. Accordingly, as the needle advancement assembly 134 is actuated proximally, the needle finger tab 138, needle carriage 136, or combinations thereof abuts against the guidewire finger tab 128, guidewire carriage 126, or combinations thereof and causes the introducer guidewire 120 to simultaneously retract proximally. Accordingly, the needle 130 and the introducer guidewire 120 are retracted into the body 110 of the introducer placement system 100. Advantageously, the needle and guidewire are contained within the body 110 to inhibit exposure to the clinician and prevent accidental stick injuries. Further, as shown in FIG. 4E, the blood flash tube 160, which extends along an inner surface of the guidewire housing 112 bends to accommodate the movement of the needle carriage, to which it is coupled.

Figure 4F:
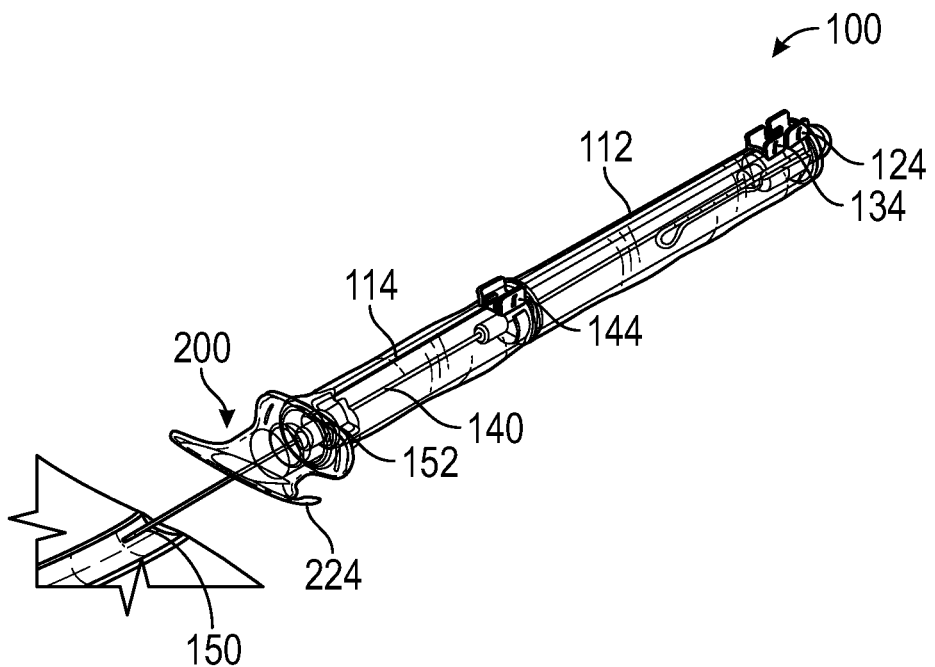
Figure 4G:
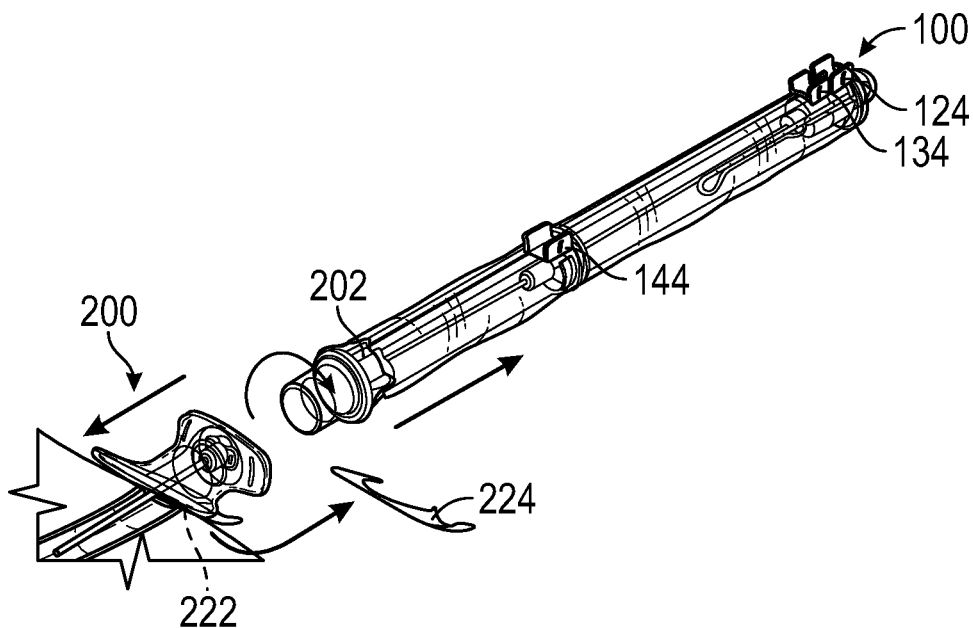

As shown in FIGS. 4F-4G, with a distal portion of the introducer 150 disposed within the vasculature 20 and the introducer hub 152 disposed within the docking station lumen 218, the dilator advancement assembly 144 can be retracted proximally to retract the dilator 140 into dilator housing 114. Advantageously, this contains the dilator 140 within the dilator housing 114 preventing exposure to the clinician.

A distal surface 216 of the docking station 200 includes an adhesive layer, as described herein. The adhesive layer 222 further includes a cover disposed thereon to protect the adhesive layer 222 during manufacture and transport. The cover 224 can be removed to expose the adhesive layer 222 and the docking station 200 can be advanced distally until a distal surface 216 contacts a skin surface of the patient, securing the docking station 200 thereto. The introducer placement system 100 can then be detached from the docking station 200, for example, by twisting and releasing the spin nut 202, leaving the introducer 150 disposed within the vasculature 20, supported by the docking station 200. Advantageously, the docking station 200 supports the introducer without the clinician having to maintain a grasp of the introducer.

Figure 4H:
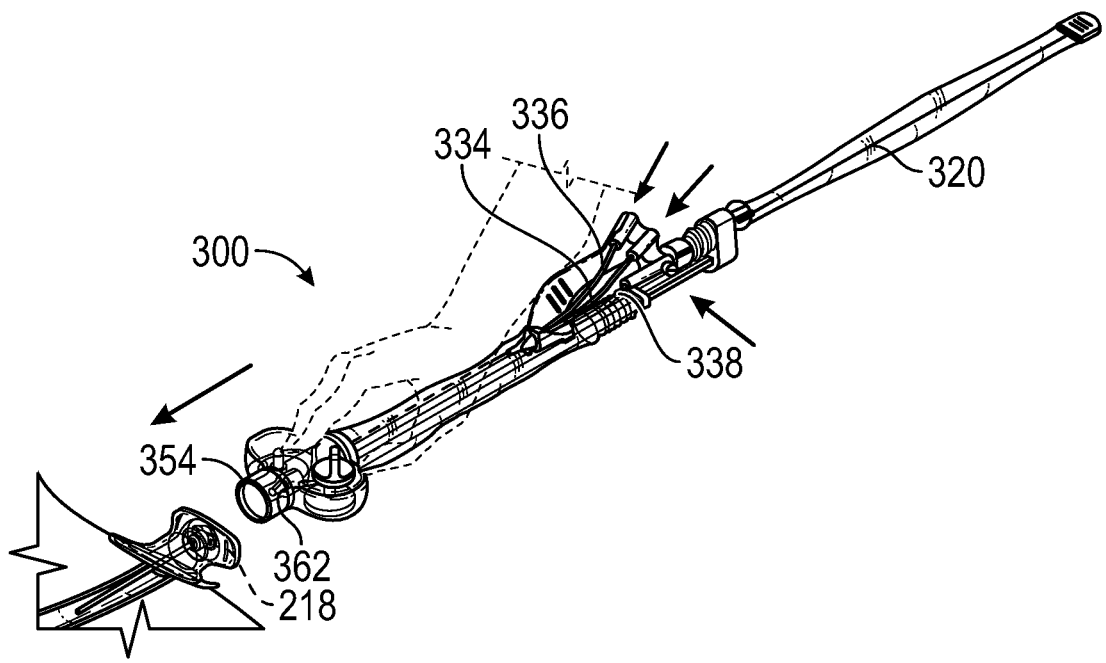
FIGS. 4H-4N show various stages of placing a catheter using the catheter placement system of FIG. 1C, in accordance with embodiments disclosed herein.

As shown in FIG. 4H, a catheter placement system 300 is provided, including a catheter 330, e.g. a triple lumen CVC catheter, as described herein. The lumens of the catheter 330 can be flushed by attaching a syringe of saline fluid, or the like to ports located at the proximal end of the extension legs 336, 338, or at a side port 386 of manifold 382. The catheter placement system 300 is then coupled with the docking station 200. The connector 354 engages a proximal portion of the docking station lumen 218 in a luer lock, or interference fit engagement, as described herein. As the connector 354 engages the docking station 200, the clamp 362 also engages the introducer hub 152 and, optionally, opens a valve disposed within the introducer hub 152.

Figure 4I:
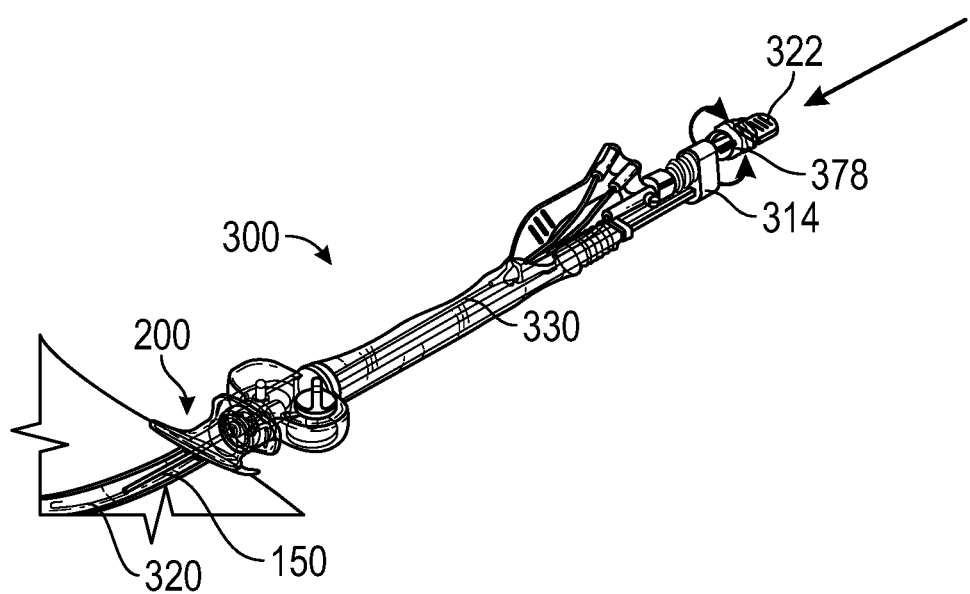

As shown in FIG. 4I, with the catheter placement system 300 coupled with the docking station 200, the catheter guidewire 320 can be advanced through the locking hub 314, through a lumen of the catheter 330, through the introducer 150, until a distal portion of the catheter guidewire 320 extends beyond a distal tip of the introducer 150, into the vasculature 20 of the patient. In an embodiment, the catheter guidewire 320 includes measurement demarcations disposed along a shaft of the catheter guidewire 320 to indicate to the clinician the length of catheter guidewire 320 disposed within the vasculature of the patient. Accordingly, the clinician can advance the catheter guidewire 320 until a distal tip thereof is disposed at a desired distance within the vasculature of the patient, proximate a target location. The clinician can then lock the catheter guidewire 320 in place using the guidewire lock 378.

Figure 4J:
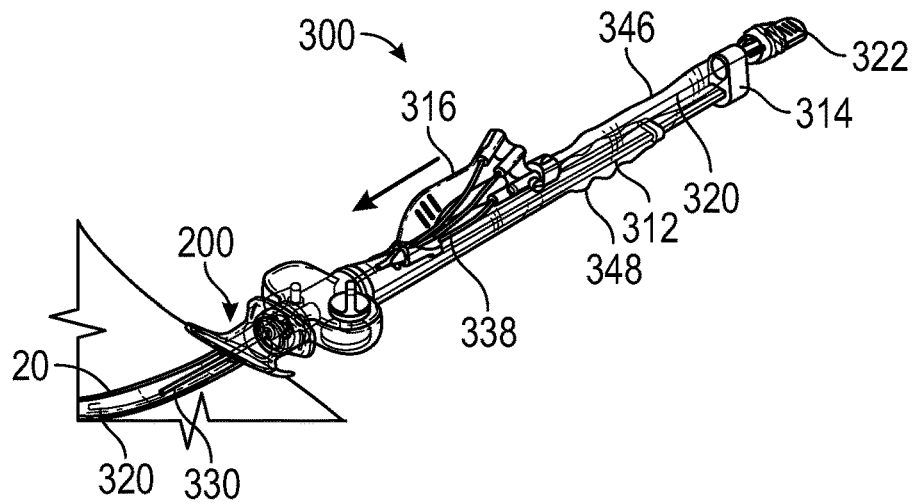

As shown in FIG. 4J, the first extension leg 334 is released from the locking hub 314 by rotating the spin nut 388. This allows the catheter frame 316, and catheter 330 coupled thereto, to slide distally along the rail 312. A clinician can grasp the catheter frame 316, e.g. at handle 318, and urge the catheter 330 distally so that a distal tip advances through the docking station lumen 218, through the clamp lumen 366, through the introducer 150 lumen and over the catheter guidewire 320 to a point that is distal of the distal tip of the introducer 150.

To note, as the catheter frame 316 is advanced, a collapsed extension leg sterile barrier 346 deploys to maintain a sterile barrier between the extension leg 338 and the locking hub 314. Similarly, the rail sterile barrier 348 allows the catheter 330 and the catheter frame 316 to slide along the rail 312 while maintaining the catheter 330 in a sterile environment.

Figure 4K:
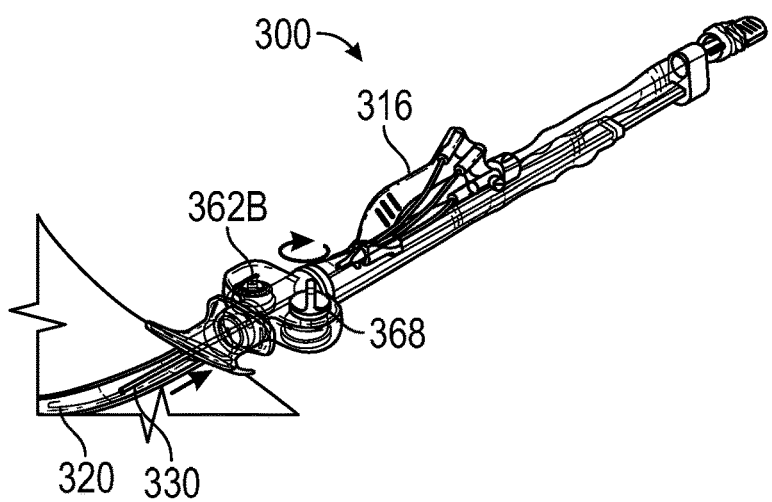

As shown in FIG. 4K, with the distal tip of the catheter 330 disposed within the vasculature 20. The introducer 150 can be retracted by twisting the knob 368. As described herein, actuating knob 368 causes the first reel 370 and the second reel 372 to rotate, withdrawing and splitting the clamp 362 into two halves, which in turn splits and retracts the introducer hub 152 into two halves that in turn splits and retracts the introducer 150 into two separate halves. Each clamp half, hub half and introducer sheath half is wound around the respective reel 370, 372 and stored within the housing 350. This removes the introducer from the insertion site while the catheter 330 remains disposed within the vasculature 20.

Figure 4L:
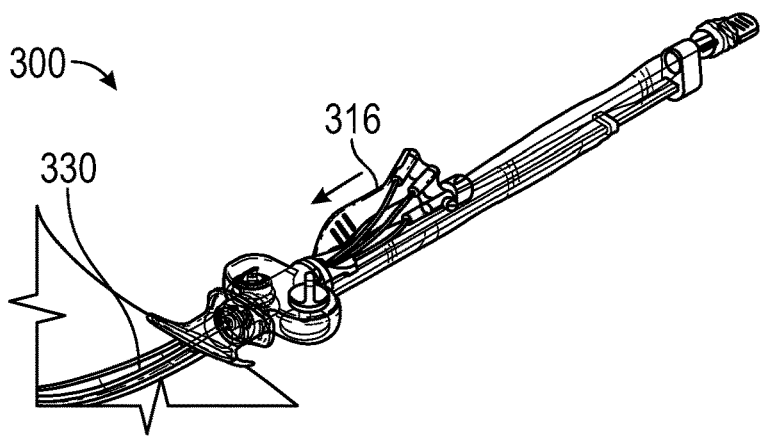
Figure 4M:
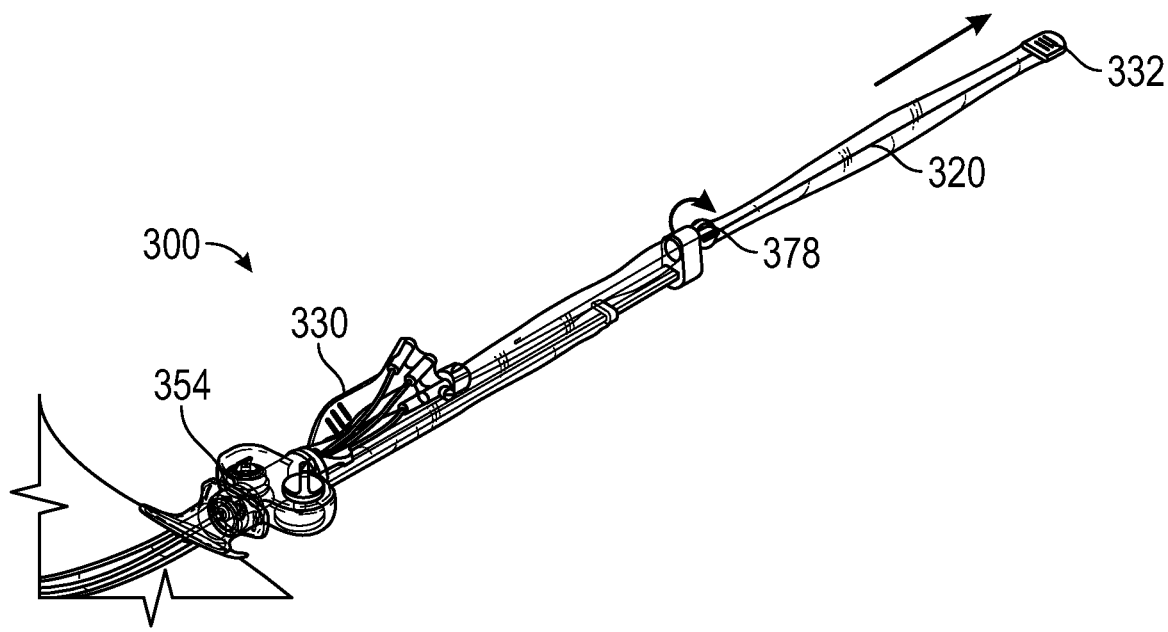

As shown in FIG. 4L, with the introducer 150 removed from the lumen 352 of the housing 350, the catheter frame 316 can be further advanced to advance the distal tip of the catheter 330 further into the vasculature of the patient. As shown in FIG. 4M, with the catheter 330 disposed further within the vasculature 20, the guidewire lock 378 can be released and the guidewire withdrawn proximally until a distal tip of the catheter guidewire 320 is withdrawn from the catheter 330. Optionally, the catheter guidewire 320 can then be locked in place again using the guidewire lock 378.

Figure 4N:
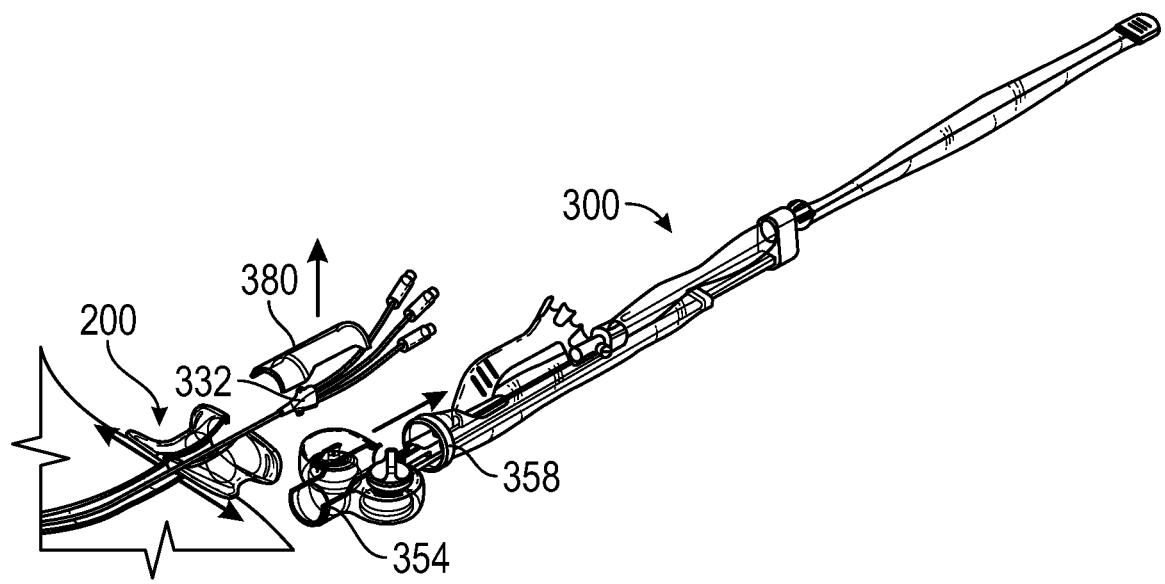

As shown in FIG. 4N, the catheter placement system 300 and docking station 200 can then be removed. The collar 358 that supports the distal end of the rail sterile barrier 348 is detached from the proximal end of the housing 350. The connector 354 is detached from the docking station 200. The housing cap 380 is detached from the housing 350 to exposed the portion of the catheter 330 disposed within the central lumen 352 of the housing 350. The catheter hub 332 is detached from catheter frame 316, and the extension legs 334, 336, 338 are detached from the respective clips 324, 326, 328 to allow the extension legs to be drawn through the collar 358. The catheter placement system 300 can then be removed from the catheter 330.

The docking station 200 is then removed from the insertion site by urging the first body portion 212 and the second body portion 214 laterally outward. The two body portions can separate along a breach-line, to allow the docking station 200 to be removed. The catheter 330 can then be stabilized against the skin surface of the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapid insertion central catheter system, comprising:
   an introducer placement system configured to place an introducer within a vasculature of a patient, comprising:
   a needle defining a needle lumen;
   an introducer guidewire, disposed within the needle lumen;
   a dilator defining a dilator lumen;
   the introducer supported by an introducer hub, the introducer defining an introducer lumen configured to receive the dilator disposed therein;
   a guidewire housing including a guidewire advancement assembly coupled to a proximal end of the introducer guidewire, and a needle retraction assembly coupled to a proximal end of the needle;
   a dilator housing coupled to a distal end of the guidewire housing and including a dilator advancement assembly coupled to a proximal end of the dilator; and
   a blood flash indicator tube fluidly coupled with the needle lumen;
   a docking station, releasably coupled to a distal end of the dilator housing, the docking station defining a lumen configured to retain the introducer hub; and
   a catheter placement system configured to engage a proximal end of the docking station and place a catheter within the vasculature of the patient, the catheter placement system comprising:
   a docking portion configured to engage the docking station to axially align the catheter with the introducer lumen;
   a rail extending proximally from the docking portion;
   a locking hub disposed at a proximal end of the rail, the locking hub defining a locking hub lumen;
   a catheter guidewire including a guidewire hub permanently attached to a distal end thereof, wherein a portion of the catheter guidewire is disposed within the locking hub lumen; and
   a catheter frame slidably engaged with the rail, wherein the catheter is supported by the catheter frame.

2. The rapid insertion central catheter system according to claim 1, wherein the introducer placement system further includes a blood flash actuator configured to release a vacuum disposed within the blood flash indicator tube to draw a proximal blood flow through the needle lumen and into the blood flash indicator tube.

3. The rapid insertion central catheter system according to claim 2, wherein the proximal blood flow disposed within the blood flash indicator tube is observable through the blood flash indicator tube and through the guidewire housing.

4. The rapid insertion central catheter system according to claim 1, wherein one of the rail and the catheter guidewire is disposed within a collapsible sterile barrier to prevent contact therewith.

5. The rapid insertion central catheter system according to claim 1, wherein the catheter is disposed within a collapsible sterile barrier that includes the rail disposed therein, the catheter frame extending through an aperture disposed in a side wall of the collapsible sterile barrier and configured to be grasped by a clinician.

6. The rapid insertion central catheter system according to claim 1, wherein one of the guidewire advancement assembly, the needle retraction assembly, and the dilator advancement assembly includes a release mechanism that requires a pair of finger tabs to move laterally inward prior to allowing any longitudinal movement thereof.

7. The rapid insertion central catheter system according to claim 1, wherein the introducer guidewire is configured to blunt a tip of the needle when the introducer guidewire is advanced distally through the needle lumen.

8. The rapid insertion central catheter system according to claim 1, wherein distal advancement of the dilator advancement assembly causes the dilator and the introducer to advance distally over the needle and the introducer guidewire.

9. The rapid insertion central catheter system according to claim 1, wherein proximal withdrawal of the needle retraction assembly causes proximal withdrawal of the needle and the introducer guidewire.

10. The rapid insertion central catheter system according to claim 1, wherein distal advancement of the dilator advancement assembly transfers the introducer from the dilator housing to the docking station.

11. The rapid insertion central catheter system according to claim 10, wherein proximal withdrawal of the dilator advancement assembly causes proximal withdrawal of the dilator from the introducer lumen.

12. The rapid insertion central catheter system according to claim 1, wherein the docking station defines a distal surface including an adhesive layer configured to adhere the docking station to a skin surface of the patient.

13. The rapid insertion central catheter system according to claim 1, wherein a width of the guidewire hub of the catheter guidewire is greater than a width of the locking hub lumen to prevent a proximal end of the catheter guidewire passing through the locking hub lumen.

14. The rapid insertion central catheter system according to claim 1, wherein the docking portion of the catheter placement system includes an introducer retraction assembly configured to split the introducer along a longitudinal axis into a first half and a second half, the first half wound around a first reel and the second half wound around a second reel.

15. The rapid insertion central catheter system according to claim 1, wherein the locking hub further includes a guidewire lock, configured to lock the catheter guidewire and prevent longitudinal movement thereof, relative to the locking hub.

16. The rapid insertion central catheter system according to claim 1, wherein the docking station includes a breach line extending longitudinally, and is configured to separate along the breach line when a first body portion and a second body portion of the docking station are urged laterally outward.

17. A rapid insertion central catheter system for placing a catheter within a vasculature of a patient, comprising:
an introducer placement system, including a dilator and an introducer having an introducer hub, the introducer placement system configured to place a distal portion of the introducer within the vasculature of the patient;
a docking station, having a proximal end releasably coupled to a distal end of the introducer placement system, and configured to receive the introducer hub from the introducer placement system as the introducer is advanced into the vasculature; and
a catheter placement system configured to engage the proximal end of the docking station, place the catheter within the vasculature of the patient, engage the introducer hub, and remove the introducer from the vasculature of the patient.

18. The rapid insertion central catheter system according to claim 17, wherein the introducer placement system includes a needle, an introducer guidewire, and a blood flash indicator tube.

19. The rapid insertion central catheter system according to claim 18, wherein the introducer placement system further includes a blood flash actuator configured to release a vacuum disposed within the blood flash indicator tube to draw a proximal blood flow through a lumen of the needle and into the blood flash indicator tube.

20. The rapid insertion central catheter system according to claim 17, wherein the catheter placement system includes one of a docking portion, a rail, a locking hub, a catheter guidewire, and a catheter frame.

21. The rapid insertion central catheter system according to claim 20, wherein one of the rail, the catheter, and the catheter guidewire is disposed within a collapsible sterile barrier to prevent contact therewith.

22. The rapid insertion central catheter system according to claim 17, wherein the introducer placement system includes one of a guidewire advancement assembly, a needle retraction assembly, and a dilator advancement assembly.

23. The rapid insertion central catheter system according to claim 22, wherein one of the guidewire advancement assembly, the needle retraction assembly, and the dilator advancement assembly includes a release mechanism.

* * * * *